US011141221B2

(12) United States Patent
Hobeika et al.

(10) Patent No.: US 11,141,221 B2
(45) Date of Patent: Oct. 12, 2021

(54) METHOD OF PREOPERATIVE PLANNING TO CORRECT SPINE MISALIGNMENT OF A PATIENT

(71) Applicant: EOS Imaging, Paris (FR)

(72) Inventors: Joe Hobeika, Besancon (FR); Lukas Vancura, Paris (FR)

(73) Assignee: EOS IMAGING, Paris (FR)

( * ) Notice: Subject to any disclaimer, the term of this patent is extended or adjusted under 35 U.S.C. 154(b) by 144 days.

(21) Appl. No.: 15/769,488

(22) PCT Filed: Nov. 19, 2015

(86) PCT No.: PCT/IB2015/002497
§ 371 (c)(1),
(2) Date: Apr. 19, 2018

(87) PCT Pub. No.: WO2017/085529
PCT Pub. Date: May 26, 2017

(65) Prior Publication Data
US 2018/0310993 A1    Nov. 1, 2018

(51) Int. Cl.
*A61B 17/70*   (2006.01)
*A61B 34/10*   (2016.01)
*A61B 6/00*    (2006.01)

(52) U.S. Cl.
CPC .............. *A61B 34/10* (2016.02); *A61B 6/505* (2013.01); *A61B 6/5217* (2013.01);
(Continued)

(58) Field of Classification Search
CPC ... A61B 17/7011–7013; A61B 17/7083–7088; A61B 17/88;
(Continued)

(56) References Cited

U.S. PATENT DOCUMENTS 5,172,695 A * 12/1992 Cann ...................... G16H 50/50
600/407
5,400,800 A *  3/1995 Jain ....................... A61B 5/1116
600/595
(Continued)

FOREIGN PATENT DOCUMENTS

DE    10 2004 008870 A1    10/2004

OTHER PUBLICATIONS

International Search Report related to Application No. PCT/IB2015/002497 dated Sep. 8, 2016.

*Primary Examiner* — Eduardo C Robert
*Assistant Examiner* — Michelle C Eckman
(74) *Attorney, Agent, or Firm* — Miller, Matthias & Hull LLP

(57) ABSTRACT

This invention relates to a method of preoperative planning to correct spine misalignment of a patient, comprising a step of making a translation and a rotation, in a sagittal plane, of each vertebra of a set of several cervical and/or thoracic and/or lumbar imaged spine vertebrae, so that said set of imaged vertebrae presents afterwards, in the sagittal plane, the same cervical lordosis and/or the same thoracic kyphosis and/or the same lumbar lordosis as a model adapted for said patient, wherein it also comprises, before said step of making said translation and said rotation in a sagittal plane: a step of making a translation and a rotation, in a coronal plane, of each vertebra of said set of several cervical and/or thoracic and/or lumbar imaged spine vertebrae, so that said set of imaged vertebrae becomes straight in said coronal plane, and of making a rotation, in an axial plane, of each vertebra of said set of several cervical and/or thoracic and/or lumbar imaged spine vertebrae, so that said set of imaged vertebrae becomes axially aligned.

17 Claims, 15 Drawing Sheets

(52) U.S. Cl.
CPC ...... *A61B 17/7011* (2013.01); *A61B 17/7013* (2013.01); *A61B 2034/102* (2016.02); *A61B 2034/105* (2016.02)

(58) Field of Classification Search
CPC .............. A61B 34/10; A61B 2034/102; A61B 2034/101; A61B 2034/104; A61B 2034/105; A61B 5/407; A61B 5/1116; A61B 5/4561; A61B 6/484; A61B 2090/376; A61B 2090/3966
See application file for complete search history.

(56) References Cited

U.S. PATENT DOCUMENTS

| | | | | | |
|---|---|---|---|---|---|
| 5,582,189 | A | * | 12/1996 | Pannozzo | A61B 5/107 128/898 |
| 5,593,408 | A | * | 1/1997 | Gayet | A61B 17/7055 606/261 |
| 5,658,286 | A | * | 8/1997 | Sava | A61B 17/7013 264/4 |
| 5,797,910 | A | * | 8/1998 | Martin | A61B 17/025 606/54 |
| 6,002,959 | A | * | 12/1999 | Steiger | A61B 6/482 128/922 |
| 6,035,691 | A | * | 3/2000 | Lin | A61B 17/8863 72/212 |
| 6,235,028 | B1 | * | 5/2001 | Brumfield | A61B 17/7083 606/53 |
| 7,095,881 | B2 | * | 8/2006 | Lelong | G06T 7/593 382/132 |
| 7,391,846 | B2 | * | 6/2008 | Verdonck | A61B 6/4441 378/62 |
| 7,567,834 | B2 | * | 7/2009 | Clayton | A61B 5/06 600/424 |
| 7,657,072 | B2 | * | 2/2010 | Periaswamy | G06T 7/0012 382/128 |
| 8,014,575 | B2 | * | 9/2011 | Weiss | B60R 25/00 382/128 |
| 8,442,621 | B2 | * | 5/2013 | Gorek | A61B 34/20 600/424 |
| 8,945,133 | B2 | * | 2/2015 | Stein | A61B 5/107 600/424 |
| 8,983,813 | B2 | * | 3/2015 | Miles | A61B 34/10 703/2 |
| 9,119,671 | B2 | * | 9/2015 | Kast | A61B 17/7025 |
| 9,491,415 | B2 | * | 11/2016 | Deitz | A61B 34/20 |
| 9,547,897 | B2 | * | 1/2017 | Parent | A61B 5/4566 |
| 9,572,601 | B2 | * | 2/2017 | Stenulson | A61B 17/7001 |
| 9,576,353 | B2 | * | 2/2017 | Mahn | G06T 7/0012 |
| 9,968,408 | B1 | * | 5/2018 | Casey | G16H 50/50 |
| 10,032,296 | B2 | * | 7/2018 | Klinder | G06T 11/008 |
| 10,292,770 | B2 | * | 5/2019 | Ryan | A61B 34/10 |
| 10,292,778 | B2 | * | 5/2019 | Kostrzewski | A61B 34/70 |
| 10,405,821 | B2 | * | 9/2019 | Hansis | G06T 11/60 |
| 10,405,935 | B2 | * | 9/2019 | McGahan | A61B 17/8863 |
| 10,413,365 | B1 | * | 9/2019 | Mosnier | A61B 17/7011 |
| 10,420,480 | B1 | * | 9/2019 | Schermerhorn | A61B 5/04001 |
| 10,420,615 | B1 | * | 9/2019 | Mosnier | A61B 34/10 |
| 10,667,864 | B2 | * | 6/2020 | Feilkas | A61B 34/10 |
| 2002/0035321 | A1 | * | 3/2002 | Bucholz | A61B 5/0064 600/407 |
| 2002/0049393 | A1 | * | 4/2002 | Cook | A61B 5/103 600/594 |
| 2002/0183610 | A1 | * | 12/2002 | Foley | A61B 8/5238 600/407 |
| 2003/0060824 | A1 | * | 3/2003 | Viart | A61B 17/7002 606/262 |
| 2004/0049103 | A1 | * | 3/2004 | McFarland | A61B 5/4561 600/300 |
| 2004/0106921 | A1 | * | 6/2004 | Cheung | A61B 17/7001 606/250 |
| 2004/0122549 | A1 | * | 6/2004 | Otsuki | G05B 19/4103 700/189 |
| 2005/0033291 | A1 | * | 2/2005 | Ebara | A61B 17/7034 606/53 |
| 2005/0119593 | A1 | * | 6/2005 | Gallard | A61B 17/7074 600/594 |
| 2005/0148839 | A1 | * | 7/2005 | Shechtman | A61B 5/4561 600/407 |
| 2005/0154296 | A1 | * | 7/2005 | Lechner | A61B 17/00234 600/429 |
| 2005/0262911 | A1 | * | 12/2005 | Dankowicz | B21D 7/14 72/31.04 |
| 2006/0015030 | A1 | * | 1/2006 | Poulin | A61B 34/20 600/424 |
| 2006/0015042 | A1 | * | 1/2006 | Linial | A61B 5/107 600/594 |
| 2006/0058616 | A1 | * | 3/2006 | Marquart | A61B 90/94 600/407 |
| 2006/0110017 | A1 | * | 5/2006 | Tsai | G06T 7/0012 382/128 |
| 2006/0120583 | A1 | * | 6/2006 | Dewaele | G06T 3/0068 382/128 |
| 2006/0150699 | A1 | * | 7/2006 | Garner | A61B 17/8863 72/31.04 |
| 2006/0195090 | A1 | * | 8/2006 | Suddaby | A61B 17/7011 606/263 |
| 2006/0271050 | A1 | * | 11/2006 | Piza Vallespir | A61B 17/7085 606/86 A |
| 2007/0055178 | A1 | * | 3/2007 | Verre | G06T 7/0012 600/594 |
| 2007/0081712 | A1 | * | 4/2007 | Huang | G06T 7/33 382/128 |
| 2007/0092121 | A1 | * | 4/2007 | Periaswamy | G06T 7/12 382/128 |
| 2007/0127799 | A1 | * | 6/2007 | Reisman | G06T 7/136 382/128 |
| 2007/0191856 | A1 | * | 8/2007 | Gil | A61B 17/025 606/90 |
| 2007/0227216 | A1 | * | 10/2007 | Schalliol | B21D 7/14 72/31.04 |
| 2007/0242869 | A1 | * | 10/2007 | Luo | G06T 7/0012 382/132 |
| 2007/0287900 | A1 | * | 12/2007 | Breen | A61B 5/4528 600/407 |
| 2008/0130825 | A1 | * | 6/2008 | Fu | G06T 7/248 378/8 |
| 2008/0177203 | A1 | * | 7/2008 | von Jako | A61B 90/36 600/587 |
| 2008/0255615 | A1 | * | 10/2008 | Vittur | A61B 17/56 606/246 |
| 2008/0269805 | A1 | * | 10/2008 | Dekutoski | A61B 17/7085 606/279 |
| 2008/0287796 | A1 | * | 11/2008 | Kiraly | A61B 5/4561 600/443 |
| 2009/0024164 | A1 | * | 1/2009 | Neubardt | A61B 5/1077 606/242 |
| 2009/0087052 | A1 | * | 4/2009 | Amiot | A61B 5/1075 382/128 |
| 2009/0088803 | A1 | * | 4/2009 | Justis | A61B 17/7083 606/254 |
| 2009/0093852 | A1 | * | 4/2009 | Hynes | A61B 17/56 606/86 A |
| 2009/0149977 | A1 | * | 6/2009 | Schendel | G16H 50/50 700/98 |
| 2009/0194206 | A1 | * | 8/2009 | Jeon | C22C 19/03 148/563 |
| 2009/0204159 | A1 | * | 8/2009 | Justis | A61B 17/708 606/323 |
| 2009/0216280 | A1 | * | 8/2009 | Hutchinson | A61B 17/7038 606/279 |
| 2009/0226055 | A1 | * | 9/2009 | Dankowicz | G06T 7/593 382/128 |
| 2009/0249851 | A1 | * | 10/2009 | Isaacs | B21F 45/008 72/31.04 |
| 2009/0254097 | A1 | * | 10/2009 | Isaacs | A61B 17/7011 606/130 |
| 2009/0254326 | A1 | * | 10/2009 | Isaacs | B21D 7/063 703/11 |

(56) References Cited

U.S. PATENT DOCUMENTS

| | | | |
|---|---|---|---|
| 2009/0285466 A1* | 11/2009 | Hipp | G06T 7/0014 382/131 |
| 2010/0063420 A1* | 3/2010 | Mahn | G06T 7/0012 600/594 |
| 2010/0063548 A1* | 3/2010 | Wang | A61B 17/7002 606/279 |
| 2010/0174673 A1* | 7/2010 | Skalli | G06T 17/10 706/50 |
| 2010/0191071 A1* | 7/2010 | Anderson | G06Q 10/10 600/301 |
| 2010/0191088 A1* | 7/2010 | Anderson | A61B 34/20 600/373 |
| 2010/0217336 A1* | 8/2010 | Crawford | G16H 50/50 606/86 R |
| 2010/0222828 A1* | 9/2010 | Stad | A61B 17/8891 606/86 A |
| 2010/0249836 A1* | 9/2010 | Seme | A61B 17/7035 606/246 |
| 2010/0249844 A1* | 9/2010 | Durrani | A61B 17/7032 606/259 |
| 2010/0312103 A1* | 12/2010 | Gorek | A61B 6/547 600/425 |
| 2010/0318129 A1* | 12/2010 | Seme | A61B 17/7053 606/254 |
| 2011/0040340 A1* | 2/2011 | Miller | A61B 17/8863 606/86 A |
| 2011/0058720 A1* | 3/2011 | Lu | G06T 7/12 382/131 |
| 2011/0066188 A1* | 3/2011 | Seme | A61B 17/7014 606/264 |
| 2011/0107270 A1* | 5/2011 | Wang | G06F 19/3481 715/850 |
| 2011/0265538 A1* | 11/2011 | Trieu | B21F 1/00 72/295 |
| 2011/0270262 A1* | 11/2011 | Justis | A61B 17/8863 606/101 |
| 2011/0319938 A1* | 12/2011 | Piza Vallespir | A61B 17/7076 606/264 |
| 2012/0065687 A1* | 3/2012 | Ballard | A61B 17/7011 606/259 |
| 2012/0143090 A1* | 6/2012 | Hay | G06T 7/0014 600/587 |
| 2012/0191192 A1* | 7/2012 | Park | A61B 17/7062 623/17.11 |
| 2012/0197297 A1* | 8/2012 | Bootwala | A61B 17/7077 606/246 |
| 2012/0232802 A1* | 9/2012 | Haimerl | A61B 5/103 702/19 |
| 2013/0079680 A1* | 3/2013 | Stein | A61B 5/107 600/594 |
| 2013/0090691 A1* | 4/2013 | Zhang | A61B 17/7032 606/264 |
| 2013/0096625 A1* | 4/2013 | McClintock | B23D 31/002 606/279 |
| 2013/0172947 A1* | 7/2013 | Greenberg | A61B 17/708 606/86 A |
| 2013/0202179 A1* | 8/2013 | Illes | A61B 5/1075 382/132 |
| 2013/0207889 A1* | 8/2013 | Chang | G01P 15/00 345/156 |
| 2013/0268007 A1* | 10/2013 | Rezach | A61B 90/06 606/279 |
| 2013/0325069 A1* | 12/2013 | Pereiro de Lamo | A61B 17/7062 606/263 |
| 2013/0329979 A1* | 12/2013 | Winternheimer | G06K 9/4604 382/131 |
| 2013/0345757 A1* | 12/2013 | Stad | A61B 17/7011 606/279 |
| 2014/0046374 A1* | 2/2014 | Asaad | A61B 17/7037 606/267 |
| 2014/0076883 A1* | 3/2014 | Brailovski | A61B 17/7002 219/491 |
| 2014/0228670 A1* | 8/2014 | Justis | A61B 17/708 600/409 |
| 2014/0228860 A1* | 8/2014 | Steines | A61B 34/30 606/130 |
| 2014/0236234 A1* | 8/2014 | Kroll | A61B 17/7016 606/264 |
| 2014/0272881 A1* | 9/2014 | Barsoum | G09B 23/30 434/274 |
| 2014/0277166 A1* | 9/2014 | Brinkman | A61B 17/7083 606/279 |
| 2014/0277170 A1* | 9/2014 | Barrett | A61B 17/7085 606/279 |
| 2014/0303486 A1* | 10/2014 | Baumgartner | A61B 34/20 600/414 |
| 2014/0311203 A1* | 10/2014 | Crawford | A61B 17/8863 72/129 |
| 2014/0316420 A1* | 10/2014 | Ballard | A61B 17/7002 606/102 |
| 2014/0316475 A1* | 10/2014 | Parikh | A61B 17/7085 606/86 A |
| 2014/0323845 A1* | 10/2014 | Forsberg | A61B 5/4561 600/407 |
| 2014/0350602 A1* | 11/2014 | Seme | A61B 17/7002 606/250 |
| 2015/0039034 A1* | 2/2015 | Frankel | A61B 17/7011 606/261 |
| 2015/0100091 A1* | 4/2015 | Tohmeh | A61B 17/7083 606/279 |
| 2015/0112392 A1* | 4/2015 | Anand | A61B 17/7083 606/279 |
| 2015/0127055 A1* | 5/2015 | Dvorak | A61B 17/7038 606/279 |
| 2015/0216568 A1* | 8/2015 | Sanpera Trigueros | A61B 17/7076 606/265 |
| 2015/0278623 A1* | 10/2015 | Nikou | A61B 34/10 382/103 |
| 2015/0320471 A1* | 11/2015 | Crawford | A61B 17/8863 72/11.1 |
| 2015/0351804 A1* | 12/2015 | Kishan | A61B 17/7011 606/260 |
| 2015/0366624 A1* | 12/2015 | Kostrzewski | A61M 29/00 606/130 |
| 2016/0012182 A1* | 1/2016 | Golay | G16H 40/20 705/3 |
| 2016/0058320 A1* | 3/2016 | Chien | A61B 5/1071 600/424 |
| 2016/0081763 A1* | 3/2016 | Arealis | A61B 5/4887 600/411 |
| 2016/0089195 A1* | 3/2016 | Cordaro | A61B 17/8863 606/279 |
| 2016/0117817 A1* | 4/2016 | Seel | A61B 90/37 382/131 |
| 2016/0166335 A1* | 6/2016 | Roger | A61B 17/1703 606/130 |
| 2016/0175013 A1* | 6/2016 | Redmond | B21D 7/14 72/15.3 |
| 2016/0210374 A1* | 7/2016 | Mosnier | A61B 17/7011 |
| 2016/0235479 A1* | 8/2016 | Mosnier | G06T 7/337 |
| 2016/0235480 A1* | 8/2016 | Scholl | A61B 17/7083 |
| 2016/0235481 A1* | 8/2016 | Dorman | A61B 17/1703 |
| 2016/0242857 A1* | 8/2016 | Scholl | A61B 17/8863 |
| 2016/0354161 A1* | 12/2016 | Deitz | A61B 34/20 |
| 2017/0000568 A1* | 1/2017 | O'Neil | A61B 5/686 |
| 2017/0112539 A1* | 4/2017 | Hayes | A61B 17/7032 |
| 2017/0112575 A1* | 4/2017 | Li | G06T 7/73 |
| 2017/0119281 A1* | 5/2017 | Herrmann | A61B 5/0082 |
| 2017/0119316 A1* | 5/2017 | Herrmann | A61B 5/0071 |
| 2017/0119472 A1* | 5/2017 | Herrmann | A61B 34/10 |
| 2017/0135770 A1* | 5/2017 | Scholl | G16H 40/63 |
| 2017/0143426 A1* | 5/2017 | Isaacs | A61B 34/20 |
| 2017/0178349 A1* | 6/2017 | Ketcha | G06T 7/33 |
| 2017/0209085 A1* | 7/2017 | Le Huec | A61B 5/1071 |

(56) References Cited

U.S. PATENT DOCUMENTS

| | | | |
|---|---|---|---|
| 2017/0231709 A1* | 8/2017 | Gupta | A61B 34/25 600/424 |
| 2017/0231710 A1* | 8/2017 | Scholl | A61B 6/487 606/279 |
| 2017/0231713 A1* | 8/2017 | Siewerdsen | A61B 5/4566 382/128 |
| 2017/0238976 A1* | 8/2017 | Higaki | A61B 17/7032 |
| 2017/0252107 A1* | 9/2017 | Turner | G06N 5/04 |
| 2017/0258526 A1* | 9/2017 | Lang | A61B 17/1703 |
| 2017/0325854 A1* | 11/2017 | Rouge | B21D 7/024 |
| 2017/0340268 A1* | 11/2017 | Danielsson | A61B 6/4241 |
| 2017/0360493 A1* | 12/2017 | Zucker | B21D 7/12 |
| 2017/0360515 A1* | 12/2017 | Kozak | A61B 90/39 |
| 2018/0040147 A1* | 2/2018 | Alhrishy | A61B 6/487 |
| 2018/0070860 A1* | 3/2018 | Gupta | A61B 5/4576 |
| 2018/0092699 A1* | 4/2018 | Finley | A61B 90/37 |
| 2018/0110506 A1* | 4/2018 | Thommen | A61F 2/4611 |
| 2018/0125537 A1* | 5/2018 | Seme | A61B 17/7004 |
| 2018/0125598 A1* | 5/2018 | McAfee | A61F 2/4657 |
| 2018/0185113 A1* | 7/2018 | Gregerson | G06T 7/248 |
| 2018/0218649 A1* | 8/2018 | Wucherer | G09B 23/285 |
| 2018/0228520 A1* | 8/2018 | Bobbitt | A61B 17/7079 |
| 2018/0235828 A1* | 8/2018 | MacMahon | A61B 5/1071 |
| 2018/0271602 A1* | 9/2018 | Frey | A61B 17/7013 |
| 2018/0289396 A1* | 10/2018 | McGahan | A61B 34/25 |
| 2018/0289408 A1* | 10/2018 | McGahan | A61B 17/8863 |
| 2018/0289491 A1* | 10/2018 | McGahan | A61B 17/70 |
| 2018/0303552 A1* | 10/2018 | Ryan | G16H 50/50 |
| 2018/0317970 A1* | 11/2018 | Lomeli | A61B 90/39 |
| 2018/0368921 A1* | 12/2018 | Jeszenszky | A61B 34/25 |
| 2019/0019433 A1* | 1/2019 | Gorbunov | G09B 9/00 |
| 2019/0029757 A1* | 1/2019 | Roh | G16H 50/00 |
| 2019/0069934 A1* | 3/2019 | Mickiewicz | A61B 17/7001 |
| 2019/0090955 A1* | 3/2019 | Singh | A61B 90/39 |
| 2019/0099221 A1* | 4/2019 | Schmidt | G16H 20/40 |
| 2019/0103190 A1* | 4/2019 | Schmidt | G06T 19/20 |
| 2019/0133666 A1* | 5/2019 | Johnson | A61B 17/7013 |
| 2019/0142519 A1* | 5/2019 | Siemionow | A61B 90/36 600/408 |
| 2019/0146458 A1* | 5/2019 | Roh | G16H 50/50 700/98 |
| 2019/0167435 A1* | 6/2019 | Cordonnier | A61F 2/4455 |
| 2019/0216454 A1* | 7/2019 | Thommen | A61B 90/57 |
| 2019/0239903 A1* | 8/2019 | Park | A61B 17/155 |
| 2019/0251711 A1* | 8/2019 | Treilhard | G06T 7/0014 |
| 2019/0269459 A1* | 9/2019 | Mosnier | A61B 17/8863 |
| 2019/0269463 A1* | 9/2019 | Mosnier | A61B 17/7011 |
| 2019/0269464 A1* | 9/2019 | Mosnier | G06T 7/0012 |
| 2019/0274760 A1* | 9/2019 | Mosnier | A61B 17/7011 |
| 2019/0290364 A1* | 9/2019 | Mosnier | G06T 7/0012 |
| 2019/0290366 A1* | 9/2019 | Pettersson | A61B 34/20 |
| 2019/0320995 A1* | 10/2019 | Amiri | A61B 6/463 |
| 2019/0336179 A1* | 11/2019 | Pak | A61B 17/7032 |
| 2019/0336182 A1* | 11/2019 | Suh | A61B 17/7002 |
| 2019/0380782 A1* | 12/2019 | McAfee | A61F 2/4455 |
| 2020/0054361 A1* | 2/2020 | Peultier | A61B 17/7085 |
| 2020/0060734 A1* | 2/2020 | Hobeika | A61B 90/90 |
| 2020/0078180 A1* | 3/2020 | Casey | B33Y 80/00 |
| 2020/0085500 A1* | 3/2020 | Dace | A61B 17/7082 |
| 2020/0100841 A1* | 4/2020 | Feilkas | A61B 34/10 |
| 2020/0129240 A1* | 4/2020 | Singh | A61B 5/00 |
| 2020/0155236 A1* | 5/2020 | Chi | A61B 34/10 |

* cited by examiner

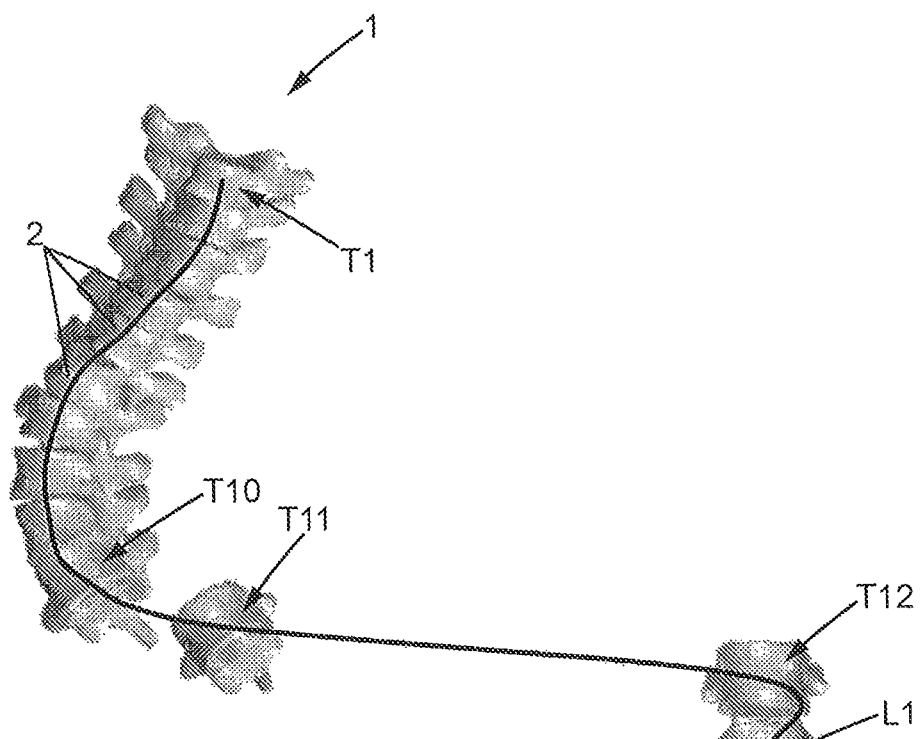
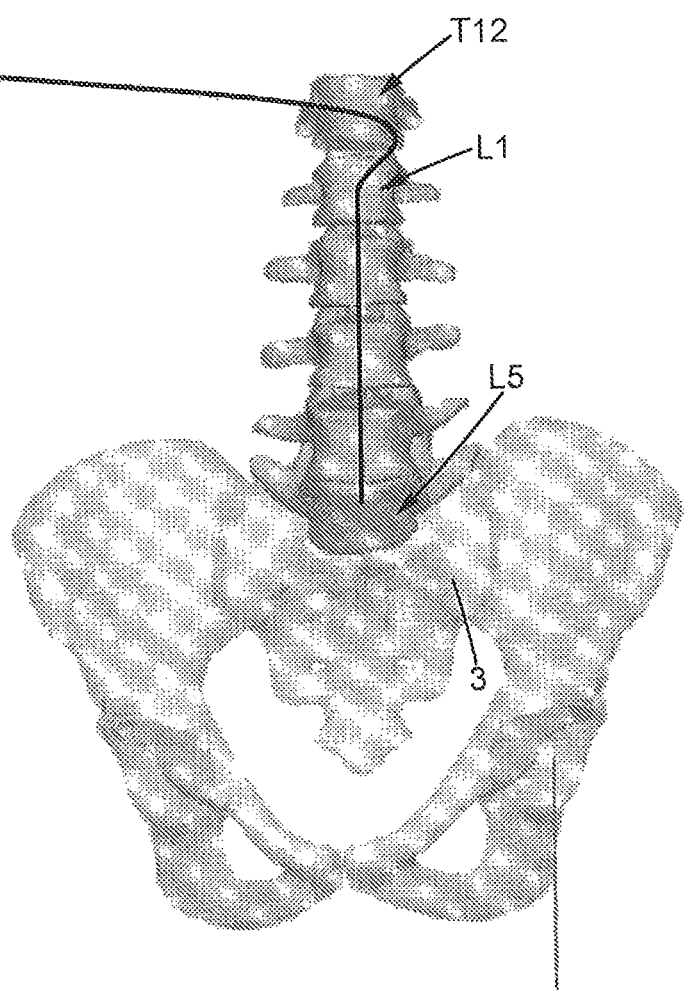
FIG. 3

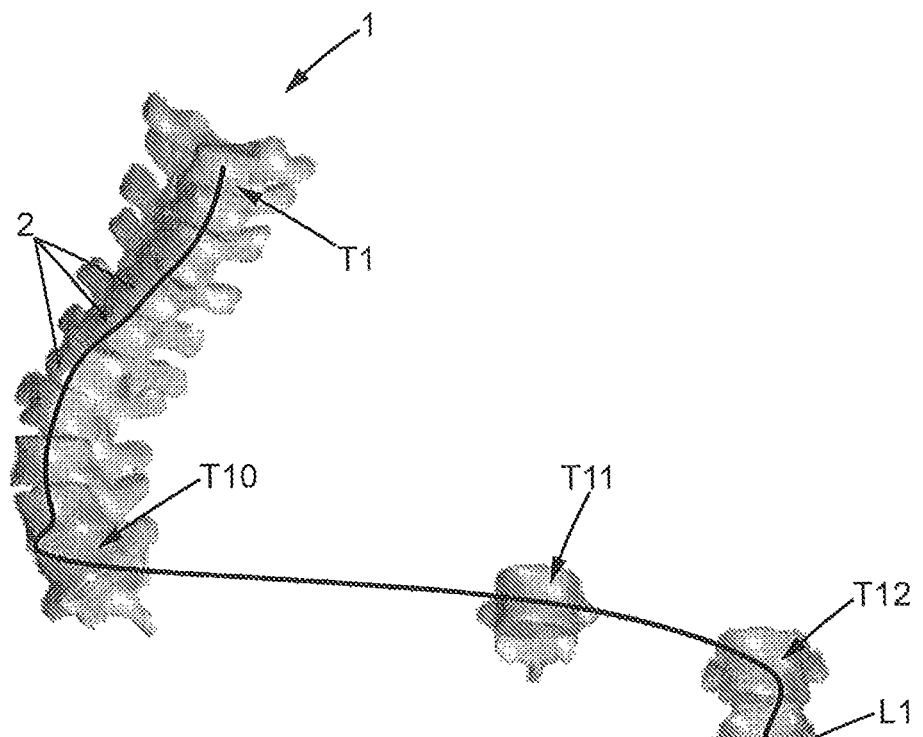
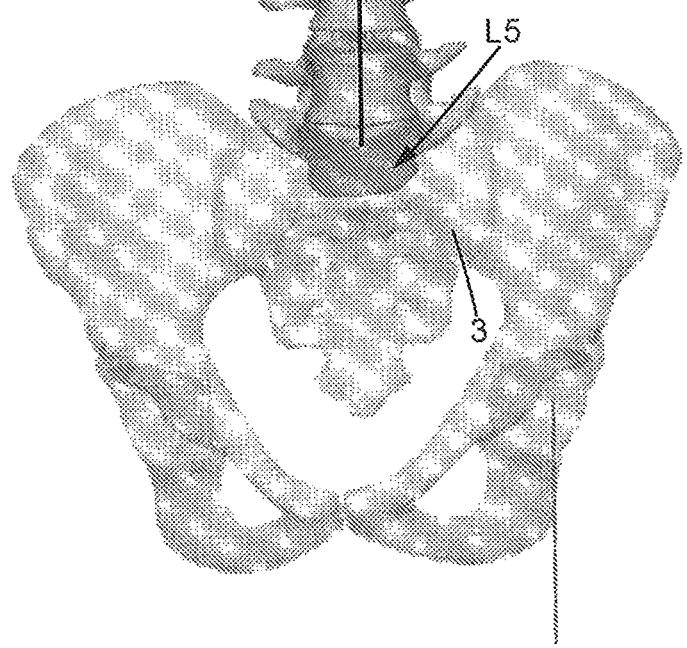
FIG. 4

METHOD OF PREOPERATIVE PLANNING TO CORRECT SPINE MISALIGNMENT OF A PATIENT

CROSS-REFERENCE TO RELATED APPLICATION

This Application is a 35 USC § 371 US National Stage filing of International Application No. PCT/IB2015/002497 filed on Nov. 19, 2015.

FIELD OF THE DISCLOSURE

The invention relates to a method of preoperative planning to correct spine misalignment of a patient and to the associated pre-shaped or pre-twisted rod, to be integrated within a patient body to support a patient spine, which has been pre-shaped or pre-twisted according to position and orientation of a set of imaged vertebrae after a step of making a translation and a rotation in a sagittal plane performed during such a method of preoperative planning to correct spine misalignment of a patient.

BACKGROUND OF THE DISCLOSURE

According to a prior art, it is known a method of preoperative planning to correct spine misalignment of a patient based on a step of making a translation and a rotation, in a sagittal plane, of each vertebra of a set of several cervical and/or thoracic and/or lumbar imaged spine vertebrae, so that said set of imaged vertebrae presents afterwards, in the sagittal plane, the same cervical lordosis and/or the same thoracic kyphosis and/or the same lumbar lordosis as a model adapted for said patient.

Unfortunately, in this prior art, the translation and rotation performed in the sagittal plane lead to an associated pre-twisted rod to be integrated within a patient body to support a patient spine, which has been pre-twisted recording to position and orientation of a set of imaged vertebrae after a step of making a translation and a rotation in a sagittal plane performed during such a method of preoperative planning to correct spine misalignment of a patient which lacks precision as to its length and as to its curvature location.

Indeed, the length of the rod is not the correct one, and if cervical lordosis and/or thoracic kyphosis and/or lumbar lordosis present correct curvatures, these curvatures are not located at the right place, specific points of these curvatures, like for example maximum points, minimum points, inflexion points, are shifted and located at the wrong parts of the vertebrae if not at the wrong vertebrae.

Therefore, during subsequent operative treatment, the surgeon will need re-twisting empirically, maybe in an iterative way, this pre-twisted rod so as to fit it correctly to the patient.

SUMMARY OF THE DISCLOSURE

The object of the present inventions is to alleviate at least partly the above mentioned drawbacks.

More particularly, the invention aims to provide for a more precise method of preoperative planning to correct spine misalignment of a patient leading to an associated pre-twisted rod presenting a more precise length and/or a more precise location of at least one of the curvatures of cervical lordosis and/or thoracic kyphosis and/or lumbar lordosis, preferably presenting a more precise length and a more precise location of at least of the curvatures of all imaged and studied spine portions among cervical lordosis and/or thoracic kyphosis and/or lumbar lordosis.

Therefore, the invention proposes, before the step of making translation and rotation in a sagittal plane of the imaged spine vertebrae, to make a translation and a rotation, in a coronal plane, of the imaged spine vertebrae so as to make them straight in the coronal plane, and a rotation, in an axial plane, of the imaged spine vertebrae so as to make them axially aligned.

This way, the step of making translation and rotation in a sagittal plane of the imaged spine vertebrae can be performed on an imaged spine already corrected from scoliosis and from axial vertebrae misalignment.

The correct cervical lordosis and/or thoracic kyphosis and/or lumbar lordosis may then be implemented on an imaged spine presenting already a straight axis in the coronal plane and an axially aligned imaged spine in the axial plane. The obtained pre-twisted rod is then much more precise, in length and/or in curvature location, having been manufactured or deformed according to a completely correctly amended imaged spine and not according to a partly correctly amended imaged spine as in prior art.

This object is achieved with a method of preoperative planning to correct spine misalignment of a patient, comprising a step of making a translation and a rotation, in a sagittal plane, of each vertebra of a set of several cervical and/or thoracic and/or lumbar imaged spine vertebrae, so that said set of imaged vertebrae presents afterwards, in the sagittal plane, the same cervical lordosis and/or the same thoracic kyphosis and/or the same lumbar lordosis as a model adapted for said patient, wherein it also comprises, before said step of making said translation and said rotation in a sagittal plane: a step of making a translation and a rotation, in a coronal plane, of each vertebra of said set of several cervical and/or thoracic and/or lumbar imaged spine vertebrae, so that said set of imaged vertebrae becomes straight in said coronal plane, and of making a rotation, in an axial plane, of each vertebra of said set of several cervical and/or thoracic and/or lumbar imaged spine vertebrae, so that said set of imaged vertebrae becomes axially aligned.

Making a translation and a rotation, in a coronal plane, of each vertebra, and making a rotation, in an axial plane, of each vertebra, may be performed either successively in two successive steps or simultaneously within the same step. When performed successively in two successive steps, the step of making a translation and a rotation, in a coronal plane, of each vertebra, may be performed before the step of making a rotation, in an axial plane, of each vertebra. When performed successively in two successive steps, the step of making a translation and a rotation, in an axial plane, of each vertebra, may be performed before the step of making a rotation, in a coronal plane, of each vertebra. Preferably, the translation in the coronal plan is performed with the first rotation, either the one in coronal plan or the one in axial plan. It is also possible, although less efficient, to perform each step separately, in whatever order, one step being a translation in coronal plan, one other step being a rotation in axial plan, still one other step being a rotation in axial plan.

This method of preoperative planning to correct spine misalignment of a patient, means that the steps of making translations and rotations, in different planes, of imaged vertebrae, are indeed steps of making translations and rotations of elements or parts of images, on a display device as for example on a screen. Only portions of images or elements within images are translated and/or rotated on a display device during this preoperative planning; no real vertebrae of a patient spine are examined, touched or moved during this preoperative planning.

This object is also achieved with a method of preoperative planning to correct spine misalignment of a patient, comprising a step of making a translation and a rotation, in a sagittal plane, of each vertebra of a set of several thoracic and/or lumbar imaged spine vertebrae, so that said set of imaged vertebrae presents afterwards, in the sagittal plane, the same thoracic kyphosis and/or the same lumbar lordosis as a model adapted for said patient, wherein it also comprises, before said step of making said translation and said rotation in a sagittal plane, successively: a step of making a translation and a rotation, in a coronal plane, of each vertebra of said set of several thoracic and/or lumbar imaged spine vertebrae, so that said set of imaged vertebrae becomes straight in said coronal plane, a step of making a rotation, in an axial plane, of each vertebra of said, set of several thoracic and/or lumbar imaged spine vertebrae, so that said set of imaged vertebrae becomes axially aligned.

Preferred embodiments comprise one or more of the following features, which can be taken separately or together, either in partial combination or in full combination.

Preferably, the method of preoperative planning to correct spine misalignment of a patient according to the invention is applied to a set of several thoracic and several lumbar imaged spine vertebrae, so that said set of imaged vertebrae presents, in the sagittal plane, the same thoracic kyphosis and the same lumbar lordosis as a model adapted for said patient. This way, the preoperative planning to correct spine misalignment of a patient and the associated pre-twisted rod will encompass a key part of patient spine, including both thoracic and lumbar vertebrae.

Preferably, the method of preoperative planning to correct spine misalignment of a patient according to the invention is applied to all thoracic and all lumbar spine vertebrae, so that said patient spine presents, in the sagittal plane, the same thoracic kyphosis and the same lumbar lordosis as a model adapted for said patient. This way, the preoperative planning to correct spine misalignment of a patient and the associated pre-twisted rod will encompass most of patient spine, including all thoracic and all lumbar vertebrae.

Preferably, in said step of making a translation and a rotation in said coronal plane, said translation and rotation are performed simultaneously, in said step of making a translation and a rotation in said sagittal plane, said translation and rotation are performed simultaneously. This is more efficient and more realistic to perform both translation and rotation of an imaged vertebra at the same time, since afterwards during operative treatment; the surgeon will perform those vertebra moves at the same time on the real vertebrae of the patient spine to effectively correct this patient spine misalignment.

Preferably, the method of preoperative planning to correct spine misalignment of a patient according to the invention also comprises, after said steps of making translations and rotations: a step of pre-twisting at least one rod, to be integrated within said patient body to support said patient spine, according to position and orientation of said set of imaged vertebrae after said step of making said translation and said rotation in a sagittal plane. Indeed, knowing position and orientation both of the misaligned starting imaged spine and of the corrected final imaged spine, the length and curvature(s) of the needed rod, to maintain corrected spine in its corrected position and orientation after such correction has been performed by the surgeon, can be deduced therefrom. Then, manufacturing or twisting a pre-manufactured rod so as to make it a pre-twisted rod can be performed according to the deduced length and curvature(s).

Preferably, in said step of pre-twisting, two rods are pre-twisted which are to be integrated respectively on both sides of said patient spine.

Preferably, the method of preoperative planning to correct spine misalignment of a patient according to the invention also comprises, after said steps of making translations and rotations: a step of editing a pattern of at least one pre-twisted rod to be integrated within said patient body to support said patient spine, according to position and orientation of said set of imaged vertebrae after said step of making said translation and said rotation in a sagittal plane. With the help of this pattern, starting from a standard rod, either the surgeon or a craftsman can make the dedicated pre-twisted rod(s) to be integrated on the patient spine and preferably on both sides of the patient spine.

Preferably, the method of preoperative planning to correct spine misalignment of patient according to the invention also comprises, after said steps of making translations and rotations: a step of calculating the length of at least one rod, to be integrated within said patient body to support said patient spine, according to position and orientation of said set of imaged vertebrae after said step of making said translation and said rotation in a sagittal plane. Calculating the exact length is very interesting, because if somewhat too short, the pre-twisted rod will not be as efficient as expected to maintain the corrected position and orientation of patient spine.

Preferably, said set of several thoracic and/or lumbar imaged spine vertebrae is a 3D spine image reconstructed from two 2D radiographic spine images, preferably from a coronal image and a sagittal image. This way, starting from only 2D radiographic spine imaging, a performing 3D preoperative planning can be made on patient spine, leading to a performing pre-twisted rod correctly deformed in the three dimensional space.

Preferably, lumbar lordosis position is obtained by moving two end markers corresponding respectively to higher extreme lumbar vertebra and sacral plate and lumbar lordosis curvature is obtained by moving an intermediate marker corresponding to an intermediate lumbar vertebra located between both extreme lumbar vertebrae, and/or thoracic kyphosis position is obtained by moving two end markers corresponding respectively to both extreme thoracic vertebrae, and thoracic kyphosis curvature is obtained by moving an intermediate marker corresponding to an intermediate thoracic vertebra located between both extreme thoracic vertebrae, and/or cervical lordosis position is obtained by moving two end markers corresponding respectively to both extreme cervical vertebrae and cervical lordosis curvature is obtained by moving an intermediate marker corresponding to an intermediate cervical vertebra located between both extreme cervical vertebrae. Such techniques using two end markers and an intermediate marker lead to an optimized compromise between the precision of the curvature(s) implemented and the complexity, both in programing for the planning tool and in manipulation in display for the surgeon, rising with the number of markers. More than three markers, so two end markers and two or more intermediate markers are also possible, but this makes the system more complex for little improved precision.

Preferably, said model is adapted for said patient first by getting an adapted lordosis from one or more patient based parameters and second by getting an adapted kyphosis from said adapted lordosis and from one or more patient based parameters. The obtained model will be more efficient when lumbar lordosis is adapted first, and when then only, with an optimized and more or less fixed lumbar lordosis (or at most varying within a narrowly limited range), the thoracic kyphosis is adapted.

Preferably, said adapted lordosis is obtained from patient pelvic incidence and from patient population type and preferably also from patient age. This leads to an optimized compromise between the precision of the curvature(s) implemented and the complexity of calculation to get the right curvature(s).

Preferably, said adapted kyphosis is obtained from said adapted lordosis and from patient sagittal vertical axis. This leads to an optimized compromise between the precision of the curvatures) implemented and the complexity of calculation to get the right curvature(s).

Preferably, said adapted kyphosis is obtained by varying said adapted lordosis curvature within a limited range, preferably plus or minus 10 degrees, while minimizing said patient sagittal vertical axis. This flexibility, allowing to still amend the lumbar lordosis during step of thoracic kyphosis determination after step of lumbar lordosis determination has been completed, such amendment being performed within a narrowly limited range, allows for quicker and more efficient convergence of the thoracic kyphosis than the convergence which would be obtained with a completely fixed value of lumbar lordosis.

Preferably, said spinal misalignment comes from a scoliosis and/or from a degenerative spine. Those are the diseases which can be corrected thanks to the method of preoperative planning to correct spine misalignment of a patient and/or to the associated pre-twisted rod(s), both according to embodiments of the invention.

Preferably, there is a pre-twisted rod, to be integrated within a patient body to support a patient spine, which has been pre-twisted according to position and orientation of a set of imaged vertebrae after a step of making a translation and a rotation in a sagittal plane performed during a method of preoperative planning to correct spine misalignment of a patient according to the invention. This pre-twisted rod may be used afterwards directly by the surgeon during subsequent operative treatment.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 3 shows a frontal patient spine view, where a starting phase of translation and rotation, in a coronal plane, allowing performance of a step of the method of preoperative planning according to an embodiment of the invention.

FIG. 4 shows a frontal patient spine view, where an ending phase of translation and rotation, in a coronal plane, allowing performance of a step of the method of preoperative planning according to an embodiment of the invention.

DETAILED DESCRIPTION OF THE DISCLOSURE

Figure 1:
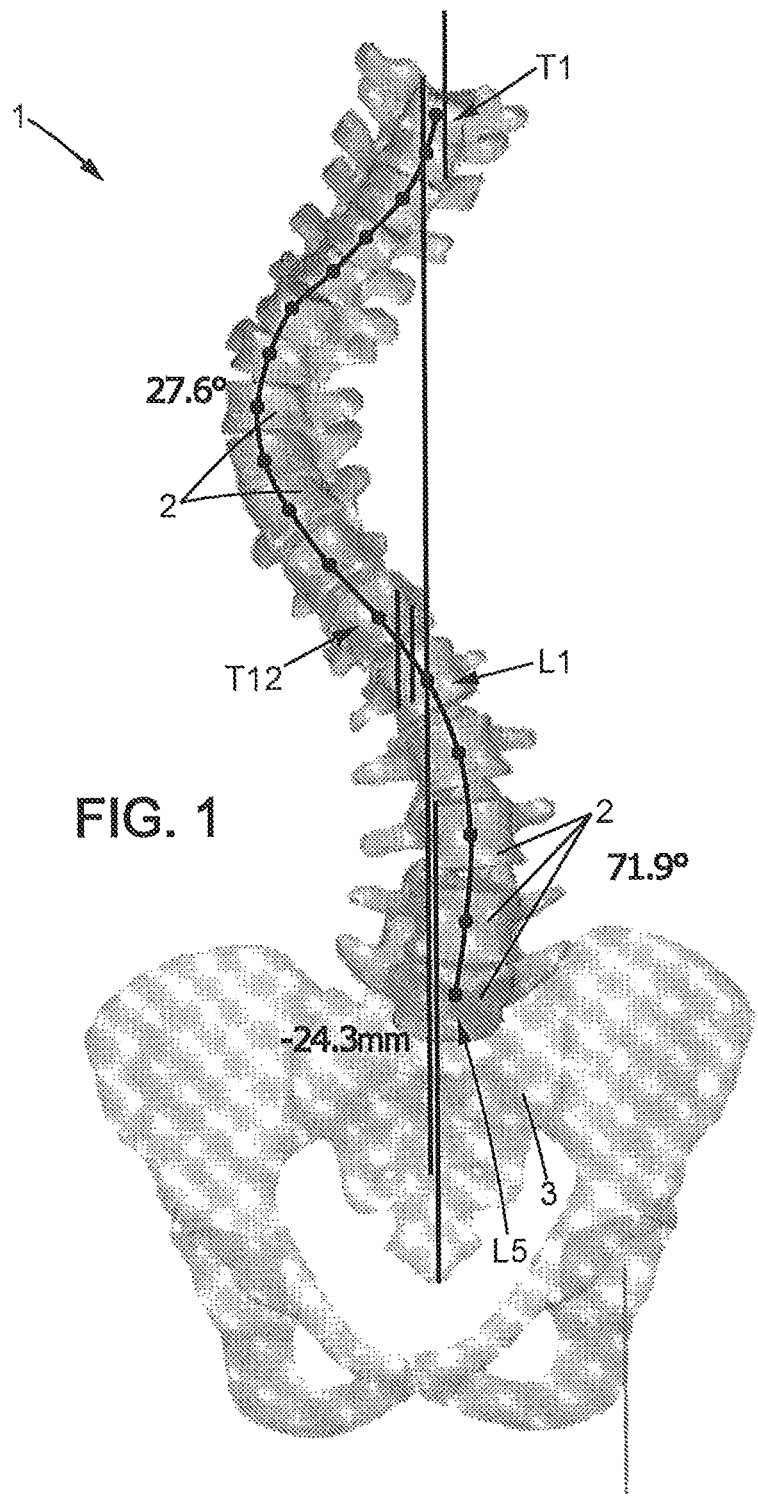
FIG. 1 shows a frontal patient spine view, the patient suffering from scoliosis, allowing performance of a step of the method of preoperative planning according to an embodiment of the invention.

FIG. 1 shows a frontal patient spine view, the patient suffering from scoliosis, allowing performance of a step of the method of preoperative planning according to an embodiment of the invention.

A patient spine 1 comprises vertebrae 2 and is ended by pelvis 3. Vertebrae 2 comprise thoracic vertebrae T1 to T12 and lumbar vertebrae L1 to L5. A sane spine 1 should appear as vertical in the coronal plan. Here, one can see that the spine 1 is heavily curved toward left of FIG. 1 in its upper part, corresponding to thoracic vertebrae 2, and slightly curved toward right of FIG. 1 in its lower part, corresponding to lumbar vertebrae 2. This means that represented spine 1 suffers from a disease called scoliosis. This means that represented spine 1 should be made straight in coronal plan. Therefore, imaged thoracic vertebrae T1 to T12 should be moved to the right of FIG. 1, whereas imaged lumbar vertebrae L1 to L5 should be moved to the left of FIG. 1.

Figure 2:
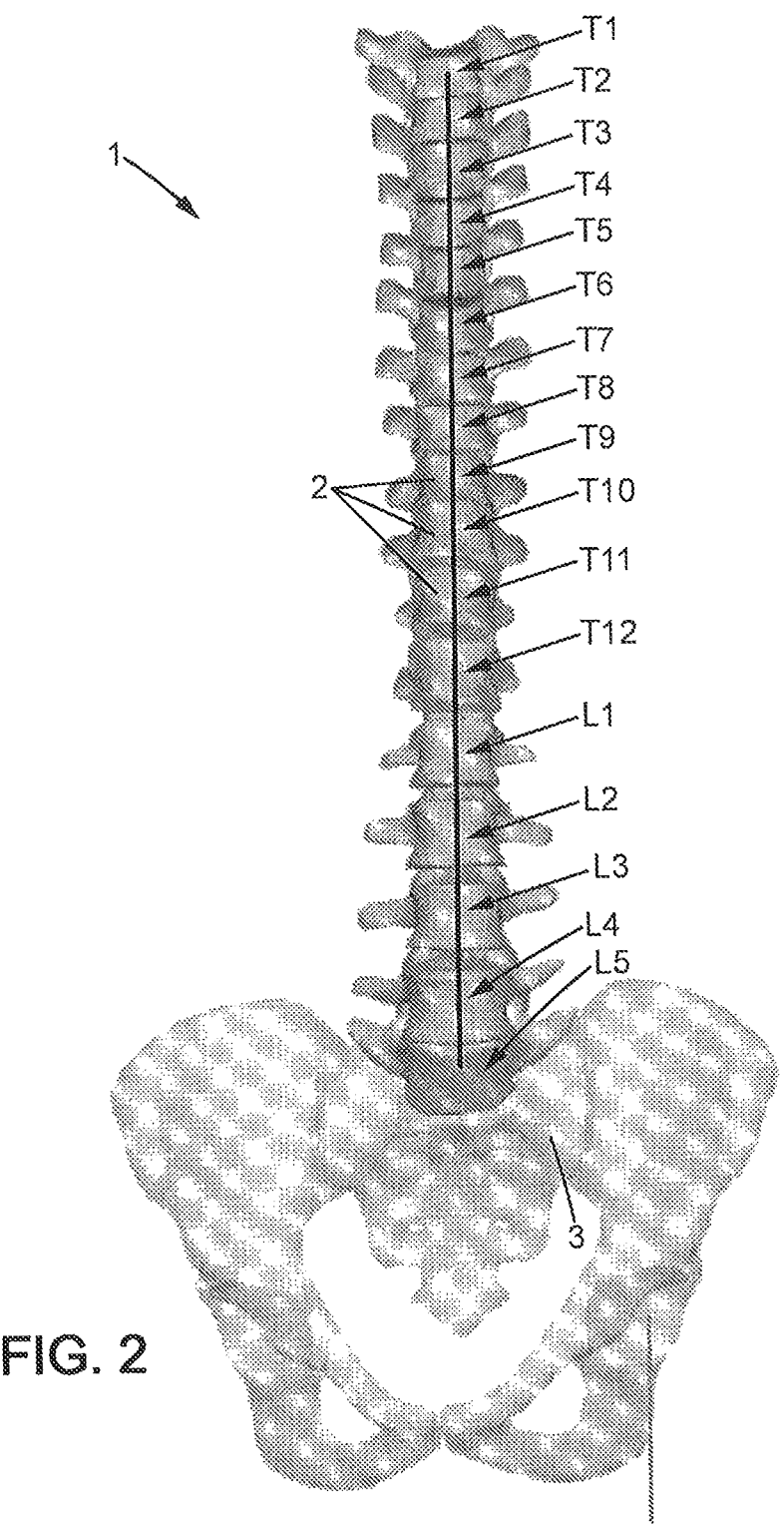
FIG. 2 shows a frontal patient spine view, the spine having been partly derotated during preoperative planning, allowing performance of a step of the method of preoperative planning according to an embodiment of the invention.

FIG. 2 shows a frontal patient spine view, the spine having been partly derotated during preoperative planning, allowing performance of a step of the method of preoperative planning according to an embodiment of the invention.

The thoracic vertebrae 2 comprise thoracic vertebrae T1, T2, T3, T4, T5, T6, T7, T8, T9, T10, T11, T12. The lumbar vertebrae 2 comprise lumbar vertebrae L1, L2, L3, L4, L5. The spine 1 is straight, what means all vertebrae 2 are vertically aligned. The represented spine 1 is a sane spine with respect to coronal plan. So, the spine 1, represented on FIG. 1, suffering from scoliosis, should be healed so as to become the straight spine 1 in coronal plan of FIG. 2, appearing to be sane with respect to coronal plan. Therefore, all imaged vertebrae 2 of FIG. 1 will have to be derotated, i.e. to undergo a derotation, so as to become straight in coronal plan as on FIG. 2. This derotation will include indeed a rotation and a translation to be performed simultaneously.

FIG. 3 shows a frontal patient spine view, where a starting phase of translation and rotation, in a coronal plane, allowing performance of a step of the method of preoperative planning according to an embodiment of the invention. During derotation, intervertebral space is maintained.

One by one, each vertebra 2 will be simultaneously translated and rotated in the coronal plan of FIG. 3, so that the spine 1 becomes straight in coronal plan of FIG. 3. On FIG. 3, lumbar vertebrae L5 to L1 and thoracic vertebra T12 have already undergone such combined translation and rotation in coronal plan and are already vertically aligned in coronal plan. Thoracic vertebra T11 has just started its combined translation and rotation in coronal plan. Thoracic vertebrae T10 to T1 are still in their original position corresponding to scoliosis of spine 1, waiting for derotation.

FIG. 4 shows a frontal patient spine view, where an ending phase of translation and rotation, in a coronal plane, allowing performance of a step of the method of preoperative planning according to an embodiment of the invention.

On FIG. 4, lumbar vertebrae L5 to L1 and thoracic vertebra T12 have already undergone such combined translation and rotation in coronal plan and are already vertically aligned in coronal plan. Thoracic vertebra T11 is about ending its combined translation and rotation in coronal plan. Thoracic vertebrae T10 to T1 are still in their original position corresponding to scoliosis of spine 1, waiting for derotation.

Figure 5:
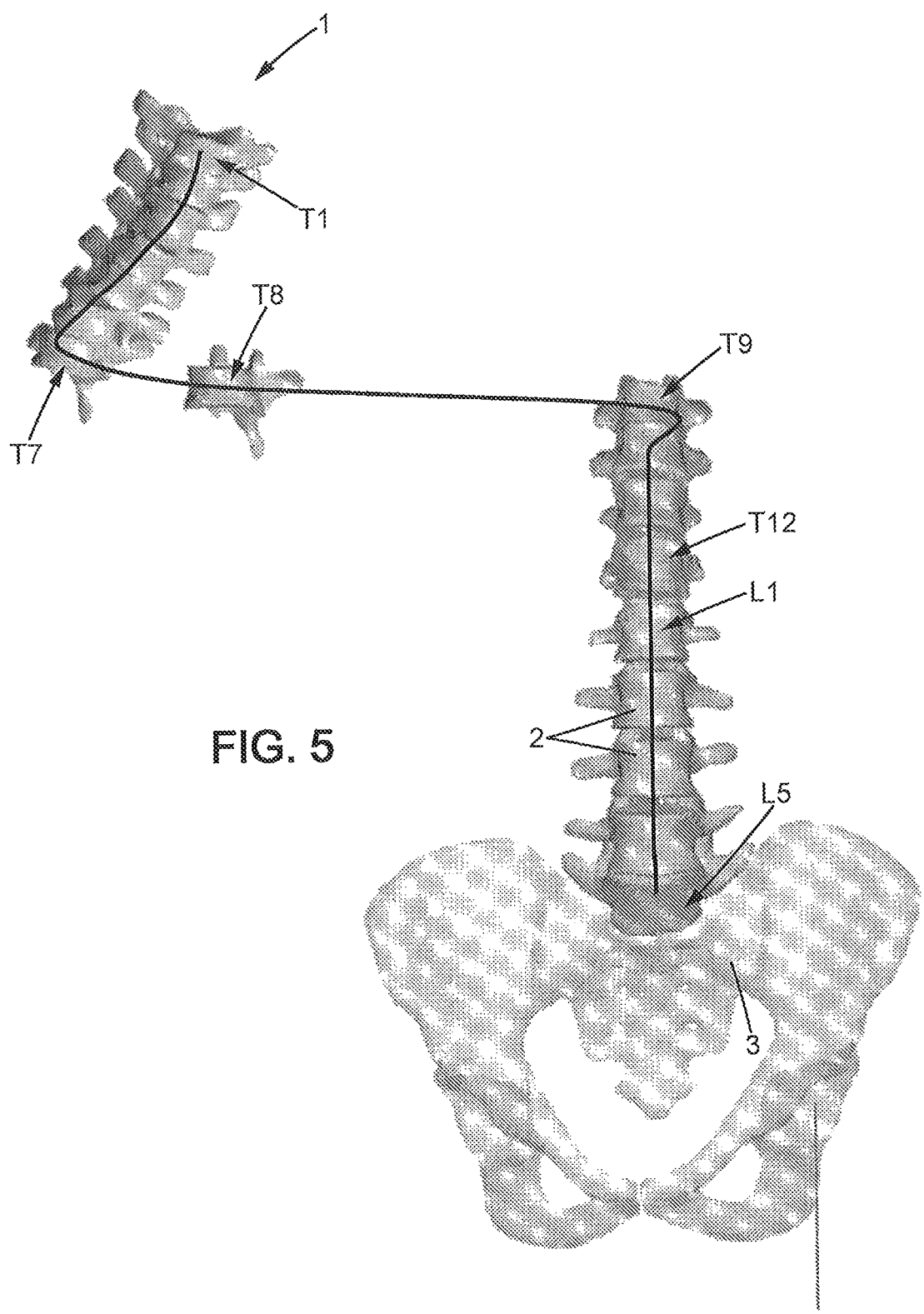
FIG. 5 shows a frontal patient spine view, where a starting phase of translation and rotation, in an axial plane, allowing performance of a step of the method of preoperative planning according to an embodiment of the invention.

FIG. 5 shows a frontal patient spine view, where a starting phase of translation and rotation, in an axial plane, allowing performance of a step of the method of preoperative planning according to an embodiment of the invention.

One by one, each vertebra 2 will be simultaneously translated and rotated in the axial plan of FIG. 5, so that the spine 2 becomes straight in axial plan of FIG. 5. On FIG. 5, lumbar vertebrae L5 to L1 and thoracic vertebrae T12 to T9 have already undergone such combined translation and rotation in axial plan and are already vertically aligned in axial plan. Thoracic vertebra T8 has just started its combined translation and rotation in axial plan. Thoracic vertebrae T7 to T1 are still in their original position corresponding to scoliosis of spine 1, waiting for derotation.

Figure 6:
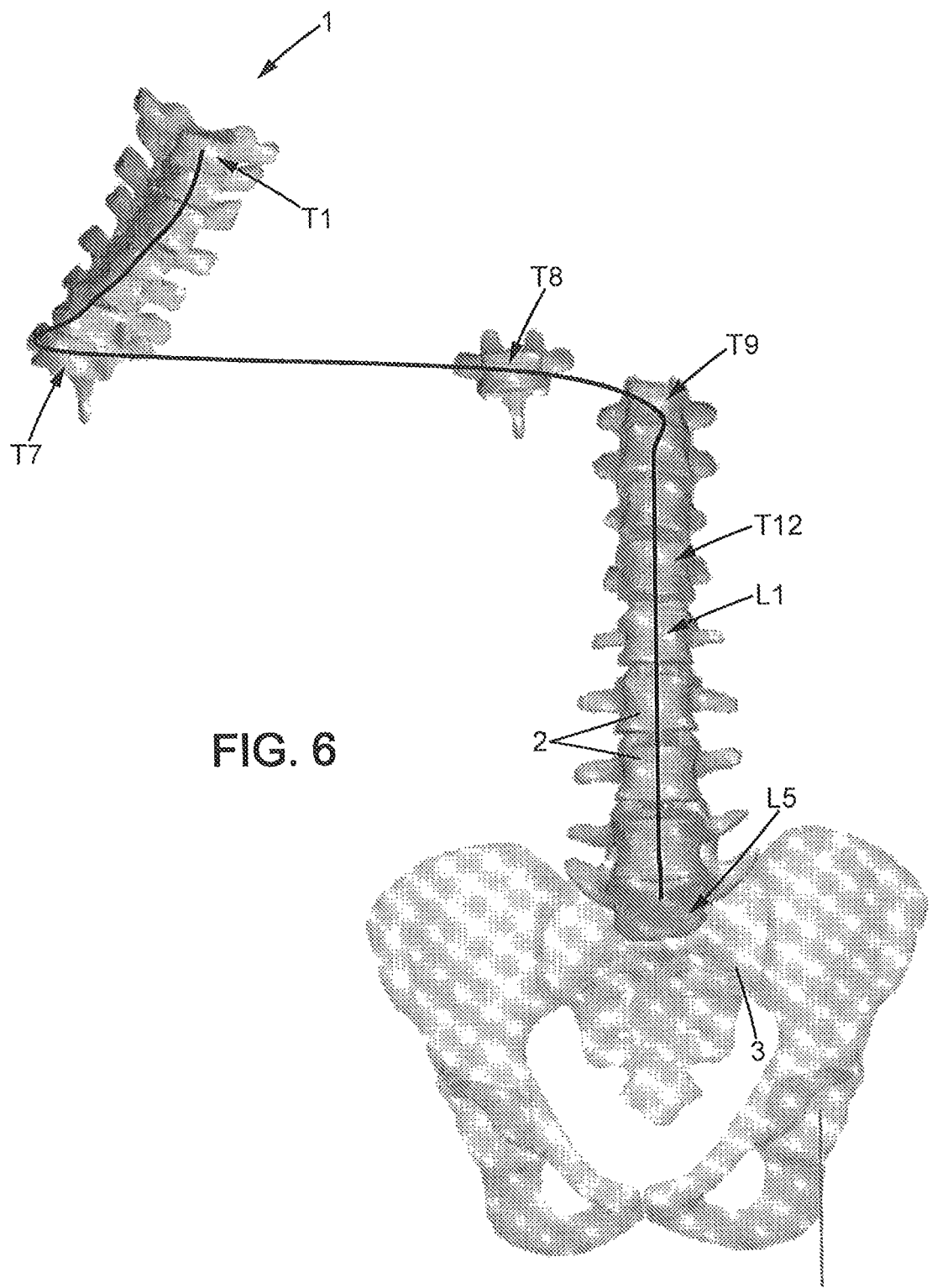
FIG. 6 shows a frontal patient spine view, where an ending phase of translation and rotation, in an axial plane, allowing performance of a step of the method of preoperative planning according to an embodiment of the invention.

FIG. 6 shows a frontal patient spine view, where an ending phase of translation and rotation, in an axial plane, allowing performance of a step of the method of preoperative planning according to an embodiment of the invention.

On FIG. 6, lumbar vertebrae L5 to L1 and thoracic vertebrae T12 to T9 have already undergone such combined translation and rotation in axial plan and are already vertically aligned in axial plan. Thoracic vertebra T8 is ending its combined translation and rotation in axial plan. Thoracic vertebrae T7 to T1 are still in their original position corresponding to scoliosis of spine 1, waiting for derotation.

FIGS. 3-6 have shown both derotations in coronal plan and in axial plan. In fact, both derotations may be performed the following way: combined translation in coronal plan and rotations respectively in coronal and axial plans are performed either successively or simultaneously with the imaged vertebrae 2 on display device during preoperative planning so that, at the end, spine 1 becomes aligned in coronal and axial plans, in a similar way as will be made with the real vertebrae later during operative treatment.

Figure 7:
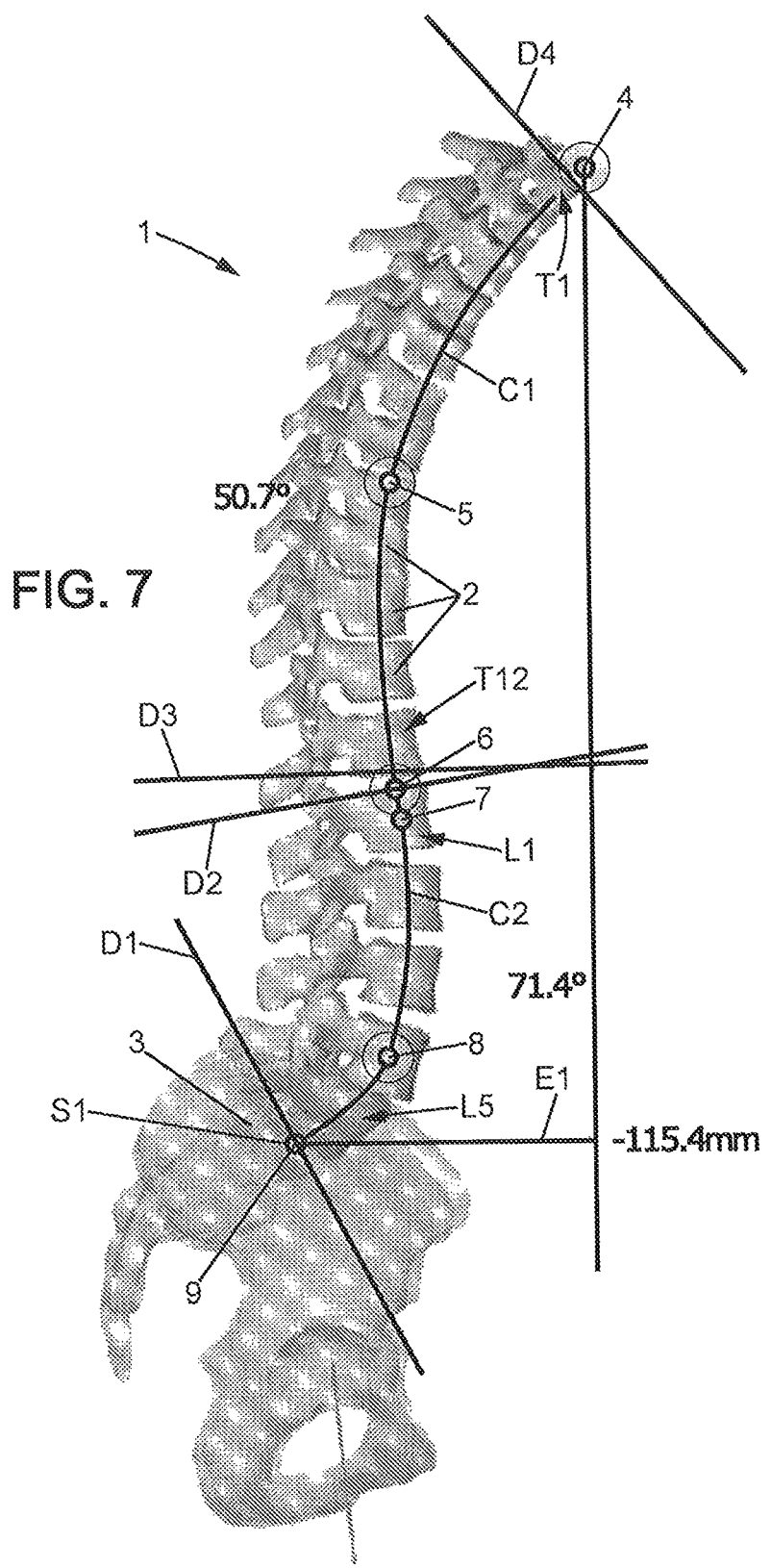
FIG. 7 shows a lateral patient spine view, with a high value of thoracic kyphosis, allowing performance of a step of the method of preoperative planning according to an embodiment of the invention.

FIG. 7 shows a lateral patient spine view, with a high value of thoracic kyphosis, allowing performance of a step of the method of preoperative planning according to an embodiment of the invention. Spine curvature should be changed so as to provide for a closer to zero (or better a close to zero) value of sagittal vertical axis.

Spine 1 is articulated on sacral plate S1 of pelvis 3 and comprises vertebrae 2 among which thoracic vertebrae T1 to T12 and lumbar vertebrae L1 to L5. The lumbar lordosis is the curvature of curve C2 of spine 1 on a subset of lumbar vertebrae L1 to L5. It can be determined as the angle between two directions D1 and D2 which correspond respectively to sacral plate S1 of pelvis orientation and to upper plate of lumbar vertebra L1 orientation. Its value on FIG. 7 is 71.4 degrees.

To change the value of lumbar lordosis, an intermediate marker 8 can be moved on the display device by the operator so as to change the curvature of curve C2 between two end markers 7 and 9 which remain fixedly respectively located on first lumbar vertebra L1 and on sacral plate S1 of pelvis 3. By moving the intermediate marker 8, the curve C2 is also displaced, since intermediate marker 8 stays on this curve C2.

The intermediate marker 8 can be moved up and down along spine 1 axis in order to change curvature distribution as well as perpendicularly to spine 1 axis in order to change curvature direction and curvature amplitude. The bounds of this intermediate marker 8 displacement are along spine 1 axis the extreme lumbar vertebrae L1 and L5, and perpendicularly to spine 1 axis the maximum amplitude corresponding to maximal curvature that the lumbar vertebrae L1 to L5 may bear without damage.

The thoracic kyphosis is the curvature of curve C1 of spine 1 on a subset of thoracic vertebrae T1 to T12. It can be determined as the angle between two directions D3 and D4 which correspond respectively to lower plate of thoracic vertebra T12 orientation and to upper plate of thoracic vertebra T1 orientation. Its value on FIG. 7 is 50.7 degrees.

To change the value of thoracic kyphosis, an intermediate marker 5 can be moved on the display device by the operator so as to change the curvature of curve C1 between two end markers 4 and 6 which remain fixedly respectively located on first thoracic vertebra T1 and on last thoracic vertebra T12 or preferably more precisely just in between last thoracic vertebra T12 and first lumbar vertebra L1. By moving the intermediate marker 5, the curve C1 is also displaced, since intermediate marker 5 stays on this curve C1.

The intermediate marker 5 can be moved up and down along spine 1 axis in order to change curvature distribution as well as perpendicularly to spine 1 axis in order to change curvature direction and curvature amplitude. The bounds of this intermediate marker 5 displacement are along spine 1 axis the extreme thoracic vertebrae T1 and T12, and perpendicularly to spine 1 axis the maximum amplitude corresponding to maximal curvature that the thoracic vertebrae T1 to T12 may bear without damage.

The sagittal vertical axis value E1 is −115.4 mm. This value should be brought close to zero, if possible and while respecting the scheduled values of lumbar lordosis and thoracic kyphosis for this specific patient, so that spine 1 becomes more balanced and may correspond to saner thoracic kyphosis and lumbar lordosis. On FIG. 7, the value of thoracic kyphosis, which is too high, should therefore be reduced.

Figure 8:
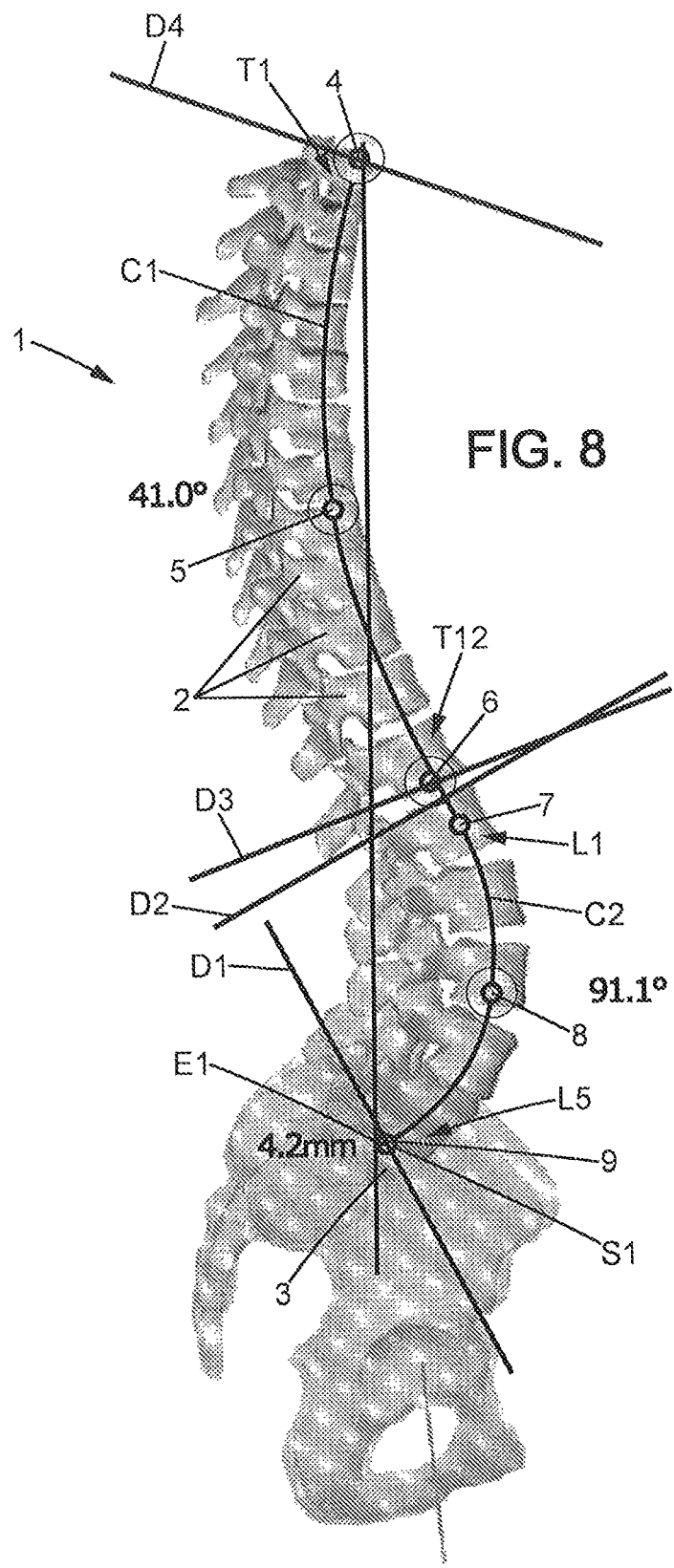
FIG. 8 shows a lateral patient spine view, with a high value of lumbar lordosis, allowing performance of a step of the method of preoperative planning according to an embodiment of the invention.

FIG. 8 shows a lateral patient spine view, with a high value of lumbar lordosis, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 8 is 91.1 degrees. To change the value of lumbar lordosis, an intermediate marker 8 can be moved on the display device by the operator so as to change the curvature of curve C2 between two end markers 7 and 9 which remain fixedly respectively located on first lumbar vertebra L1 and on sacral plate S1 of pelvis 3. By moving the intermediate marker 8, the curve C2 is also displaced, since intermediate marker 8 stays on this curve C2.

The value of thoracic kyphosis is on FIG. 8 is 41.0 degrees. To change the value of thoracic kyphosis, an intermediate marker 5 can be moved on the display device by the operator so as to change the curvature of curve C1 between two end markers 4 and 6 which remain fixedly respectively located on first thoracic vertebra T1 and on last thoracic vertebra T12 or preferably more precisely just in between last thoracic vertebra T12 and first lumbar vertebra L1. By moving the intermediate marker 5, the curve C1 is also displaced, since intermediate marker 5 stays on this curve C1.

The sagittal vertical axis value E1 is 4.2 mm. This value should be brought close to zero, if possible and while respecting the scheduled values of lumbar lordosis and thoracic kyphosis for this specific patient, so that spine 1 becomes more balanced and may correspond to saner thoracic kyphosis and lumbar lordosis. On FIG. 8, the value of lumbar lordosis, which is too high, should therefore be reduced.

Figure 9:
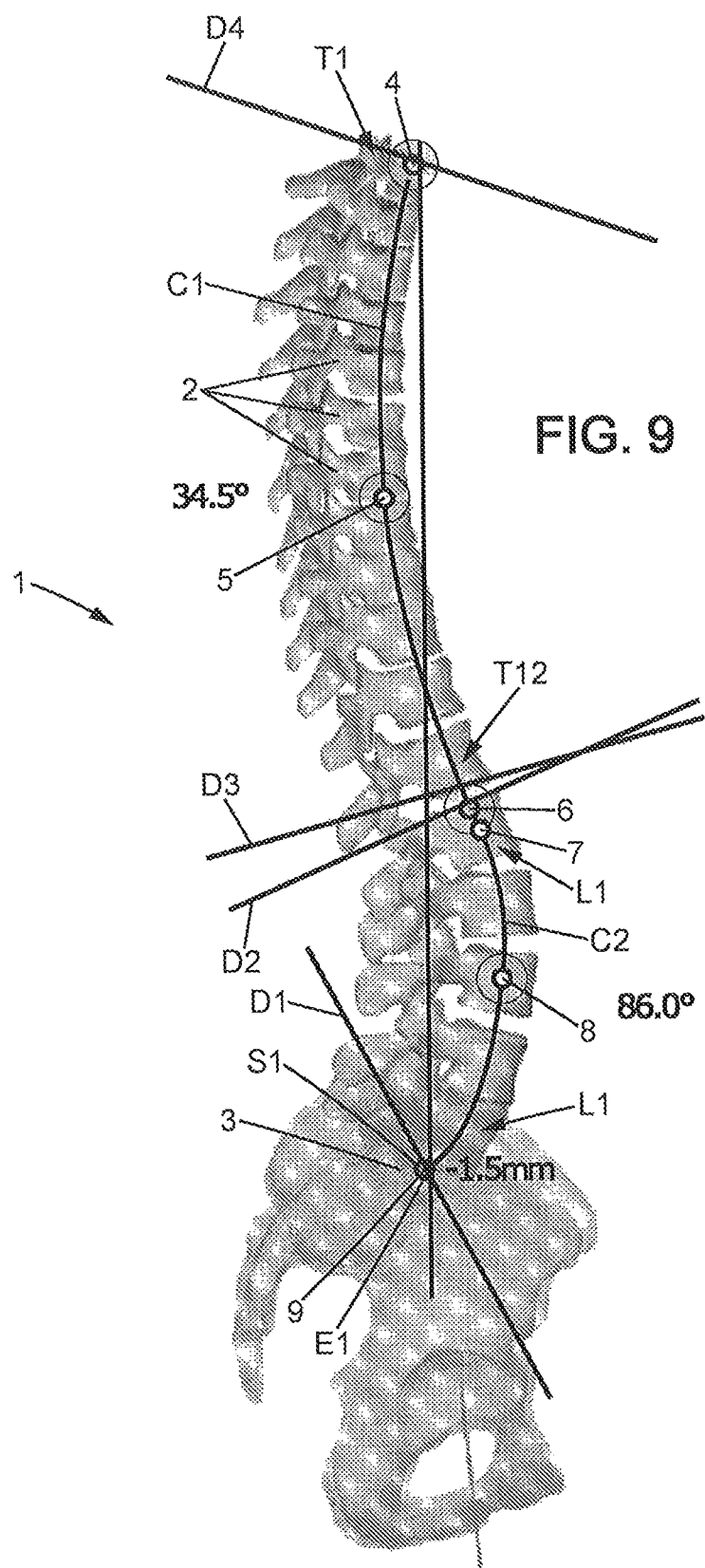
FIG. 9 shows a lateral patient spine view, with a close to zero value of sagittal vertical axis, allowing performance of a step of the method of preoperative planning according to an embodiment of the invention.

FIG. 9 shows a lateral patient spine view, with a close to zero value of sagittal vertical axis, allowing performance of a step of the method of preoperative planning according to an embodiment of the invention. Spine curvature is adapted because the value of sagittal vertical axis is already close to zero.

The value of lumbar lordosis is on FIG. 9 is 86.0 degrees. To change the value of lumbar lordosis, an intermediate marker 8 can be moved on the display device by the operator so as to change the curvature of curve C2 between two end markers 7 and 9.

The value of thoracic kyphosis is on FIG. 9 is 34.5 degrees. To change the value of thoracic kyphosis, an intermediate marker 5 can be moved on the display device by the operator so as to change the curvature of curve C1 between two end markers 4 and 6.

The sagittal vertical axis value E1 is −1.5 mm. This value is indeed very close to zero. On FIG. 9, corresponding spine 1 is well balanced and corresponds to sane thoracic kyphosis and lumbar lordosis.

Figure 10:
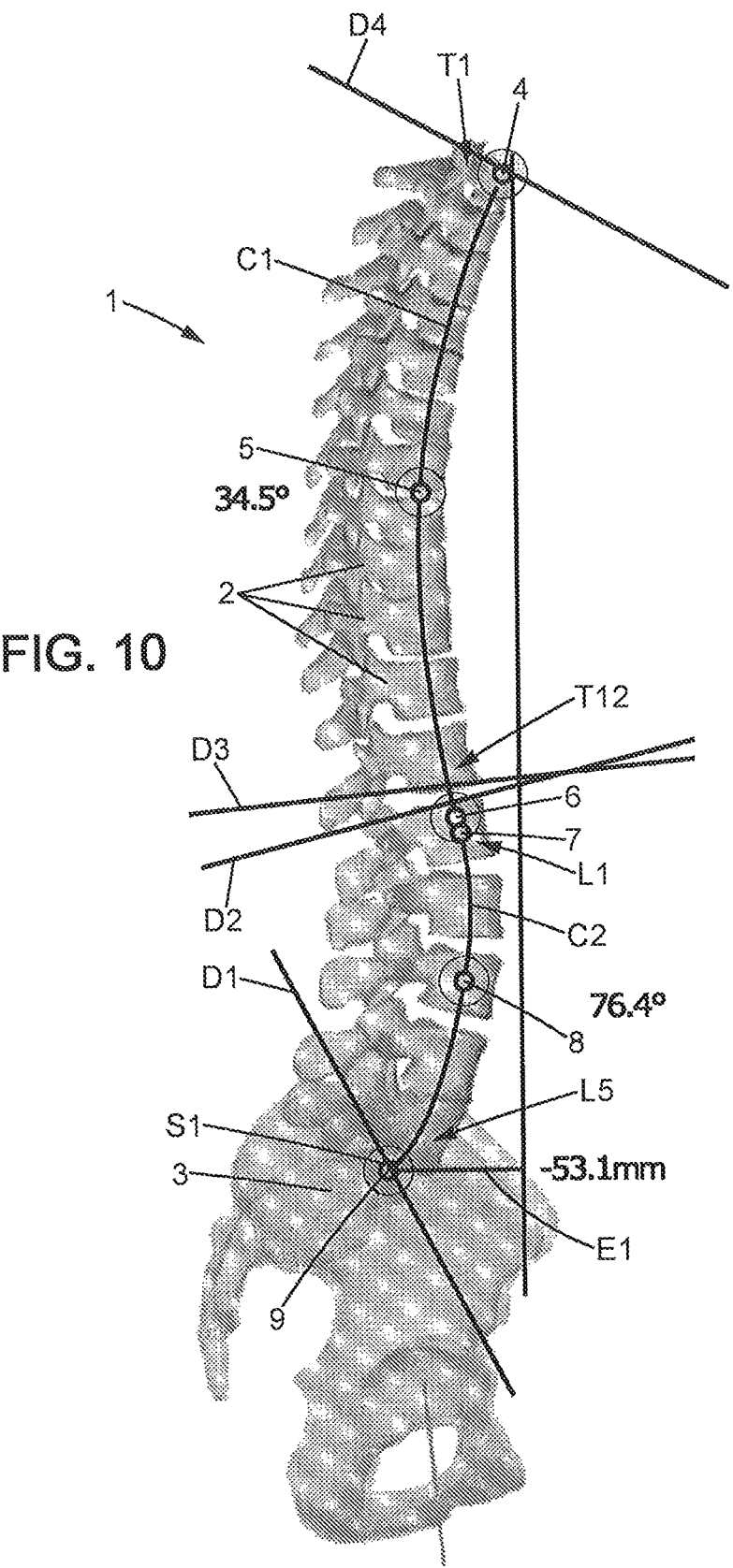
FIG. 10 shows a lateral patient spine view, with a lumbar lordosis concentrated in the middle region of lumbar vertebrae, allowing performance of a step of the method of preoperative planning according to an embodiment of the invention.

FIG. 10 shows a lateral patient spine view, with a lumbar lordosis concentrated in the middle region of lumbar vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 10 is 76.4 degrees. The lumbar lordosis is concentrated in the middle region of lumbar vertebrae 2; therefore intermediate marker 8 is halfway between end markers 7 and 9. To change the value of lumbar lordosis, intermediate marker 8 can be moved on the display device by the operator so as to change the curvature of curve C2 between two end markers 7 and 9.

The value of thoracic kyphosis is on FIG. 10 is 34.5 degrees. The thoracic kyphosis is concentrated in the middle region of thoracic vertebrae 2; therefore intermediate marker 5 is halfway between end markers 4 and 6. To change the value of thoracic kyphosis, intermediate marker 5 can be moved on the display device by the operator so as to change the curvature of curve C1 between two end markers 4 and 6.

The sagittal vertical axis value E1 is −53.1 mm. This value should be brought close to zero, if possible and while respecting the scheduled values of lumbar lordosis and thoracic kyphosis for this specific patient, so that spine 1 becomes more balanced.

Figure 11:
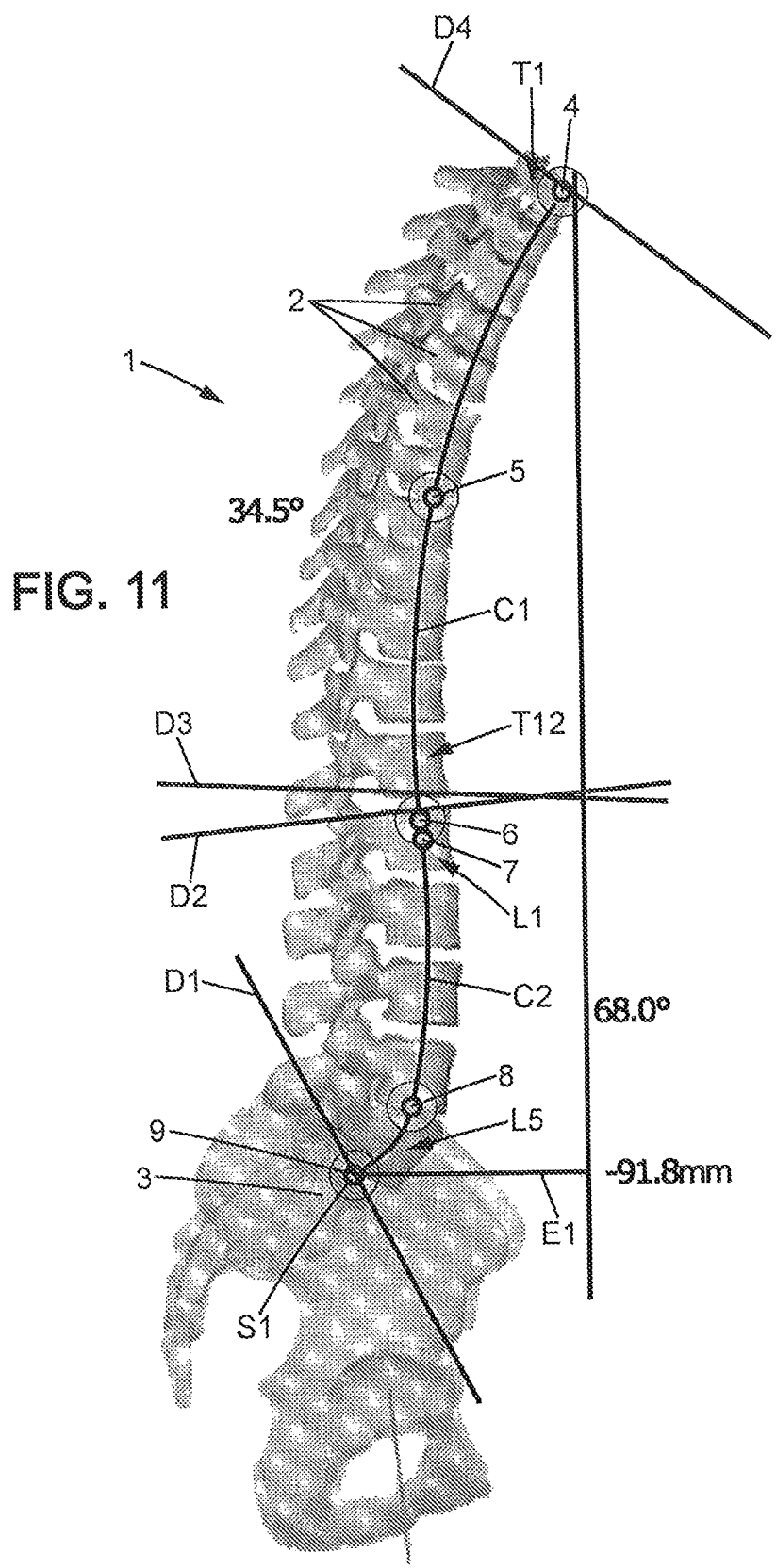
FIG. 11 shows a lateral patient spine view, with a lumbar lordosis concentrated in the lower region of lumbar vertebrae, allowing performance of a step of the method of preoperative planning according to an embodiment or the invention.

FIG. 11 shows a lateral patient spine view, with a lumbar lordosis concentrated in the lower region of lumbar vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 11 is 68.0 degrees. The lumbar lordosis is concentrated in the lower region of lumbar vertebrae 2; therefore intermediate marker 8 is closer to end marker 9 than to end marker 7. The lumbar lordosis should not be so concentrated in the lower region of lumbar vertebrae 2 and should be better distributed. To change the value of lumbar lordosis, intermediate marker 8 can be moved on the display device by the operator so as to change the curvature of curve C2 between two end markers 7 and 9.

The value of thoracic kyphosis is on FIG. 11 is 34.5 degrees. The thoracic kyphosis is concentrated in the middle region of thoracic vertebrae 2; therefore intermediate marker 5 is halfway between end markers 4 and 6. To change the value of thoracic kyphosis, intermediate marker 5 can be moved on the display device by the operator so as to change the curvature of curve C1 between two end markers 4 and 6.

The sagittal vertical axis value E1 is −91.8 mm. This value should be brought close to zero, if possible and while respecting the scheduled values of lumbar lordosis and thoracic kyphosis for this specific patient, so that spine 1 becomes more balanced.

Figure 12:
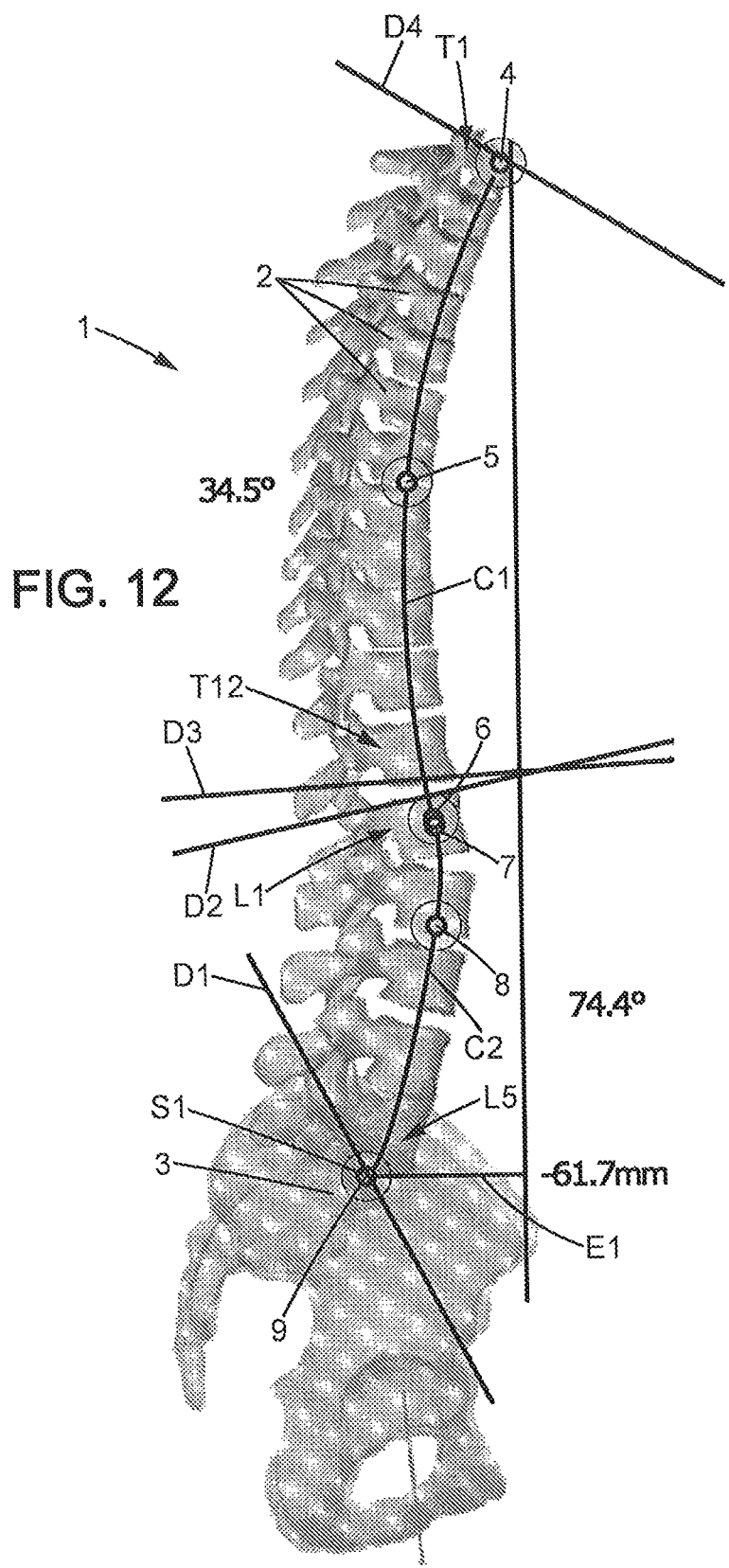
FIG. 12 shows a lateral patient spine view, with a lumbar lordosis concentrated in the upper region of lumbar vertebrae, allowing performance of a step of the method of preoperative planning according to an embodiment of the invention.

FIG. 12 shows a lateral patient spine view, with a lumbar lordosis concentrated in the upper region of lumbar vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 12 is 74.4 degrees. The lumbar lordosis is concentrated in the upper region of lumbar vertebrae 2; therefore intermediate marker 8 is closer to end marker 7 than to end marker 9. The lumbar lordosis should not be so concentrated in the upper region of lumbar vertebrae 2 and should be better distributed. To change the value of lumbar lordosis, intermediate marker 8 can be moved on the display device by the operator so as to change the curvature of curve C2 between two end markers 7 and 9.

The value of thoracic kyphosis is on FIG. 12 is 34.5 degrees. The thoracic kyphosis is concentrated in the middle region of thoracic vertebrae 2; therefore intermediate marker 5 is halfway between end markers 4 and 6. To change the value of thoracic kyphosis, intermediate marker 5 can be moved on the display device by the operator so as to change the curvature of curve C1 between two end markers 4 and 6.

The sagittal vertical axis value E1 is −61.7 mm. This value should be brought close to zero, if possible and while respecting the scheduled values of lumbar lordosis and thoracic kyphosis for this specific patient, so that spine 1 becomes more balanced.

Figure 13:
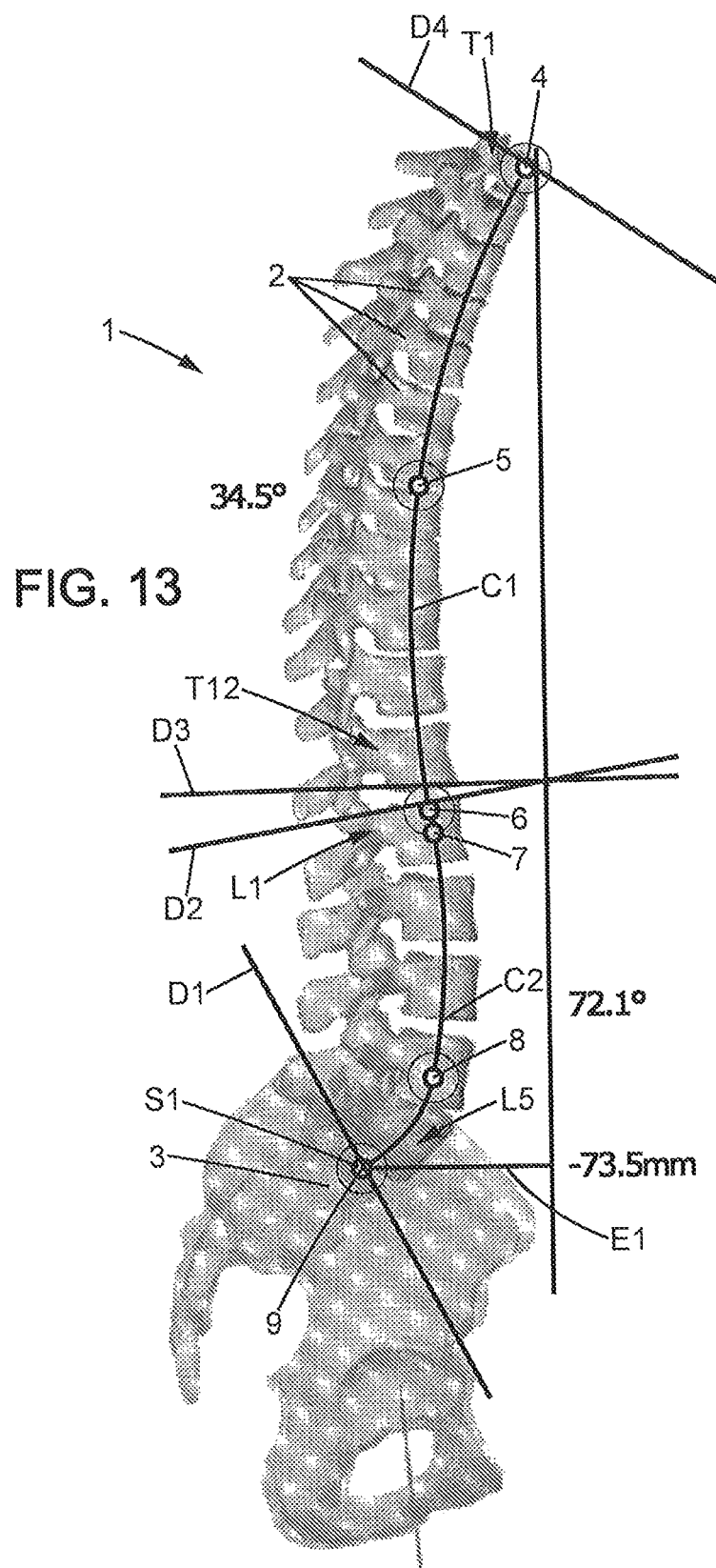
FIG. 13 shows a lateral patient spine view, with a thoracic kyphosis concentrated in the middle region of thoracic vertebrae, allowing performance of a step of the method of preoperative planning according to an embodiment of the invention.

FIG. 13 shows a lateral patient spine view, with a thoracic kyphosis concentrated in the middle region of thoracic vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 13 is 72.1 degrees. The lumbar lordosis is concentrated in the lower region of lumbar vertebrae 2; therefore intermediate marker 8 is closer to end marker 9 than to end marker 7. To change the value of lumbar lordosis, intermediate marker 8 can be moved on the display device by the operator so as to change the curvature of curve C2 between two end markers 7 and 9.

The value of thoracic kyphosis is on FIG. 13 is 34.5 degrees. The thoracic kyphosis is concentrated in the middle region of thoracic vertebrae 2; therefore intermediate marker 5 is halfway between end markers 4 and 6. To change the value of thoracic kyphosis, intermediate marker 5 can be moved on the display device by the operator so as to change the curvature of curve C1 between two end markers 4 and 6.

The sagittal vertical axis value E1 is −73.5 mm. This value should be brought close to zero, if possible and while respecting the scheduled values of lumbar lordosis and thoracic kyphosis for this specific patient, so that spine 1 becomes more balanced.

Figure 14:
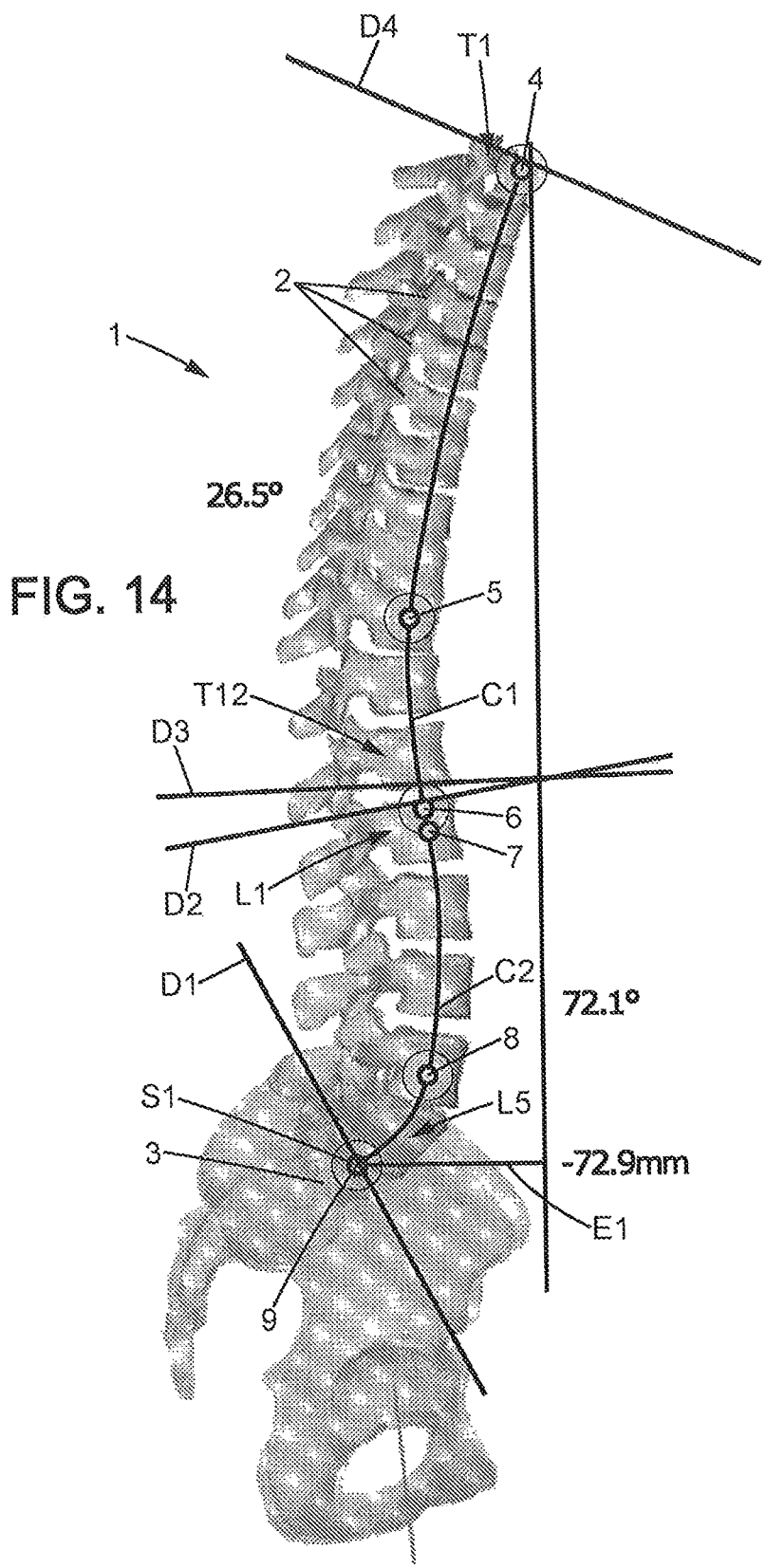
FIG. 14 shows a lateral patient spine view, with a thoracic kyphosis concentrated in the lower region of thoracic vertebrae, allowing performance of a step of the method of preoperative planning according to an embodiment of the invention.

FIG. 14 shows a lateral patient spine view, with a thoracic kyphosis concentrated in the lower region of thoracic vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 14 is 72.1 degrees. The lumbar lordosis is concentrated in the lower region of lumbar vertebrae 2; therefore intermediate marker 8 is closer to end marker 9 than to end marker 7. To change the value of lumbar lordosis, intermediate marker 8 can be moved on the display device by the operator so as to change the curvature of curve C2 between two end markers 7 and 9.

The value of thoracic kyphosis is on FIG. 14 is 26.5 degrees. The thoracic kyphosis is concentrated in the lower region of thoracic vertebrae 2; therefore intermediate marker 5 is closer to end marker 6 than to end marker 4. The thoracic kyphosis should not be so concentrated in the lower region of thoracic vertebrae 2 and should be better distributed. To change the value of thoracic kyphosis, intermediate marker 5 can be moved on the display device by the operator so as to change the curvature of curve C1 between two end markers 4 and 6.

The sagittal vertical axis value E1 is −72.9 mm. This value should be brought close to zero, if possible and while respecting the scheduled values of lumbar lordosis and thoracic kyphosis for this specific patient, so that spine 1 becomes more balanced.

Figure 15:
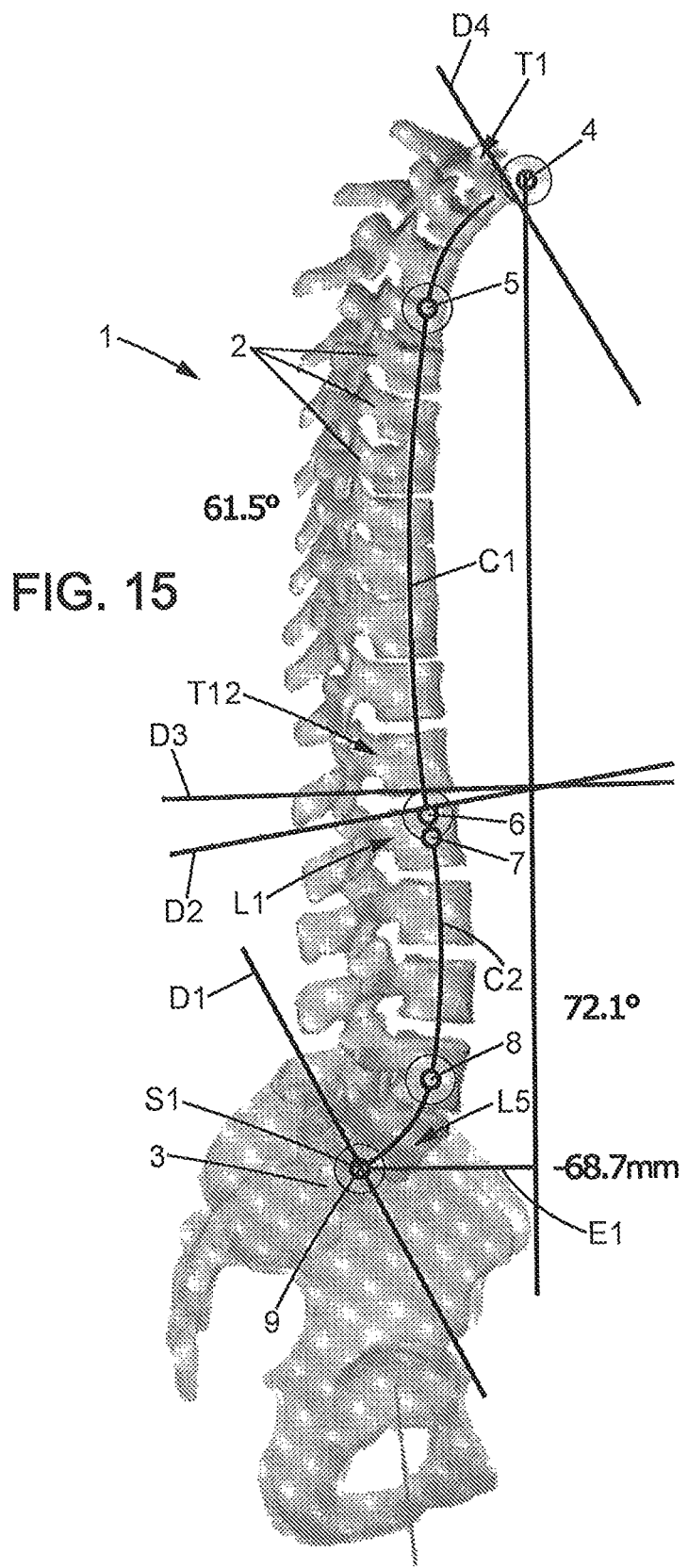
FIG. 15 shows a lateral patient spine view, with a thoracic kyphosis concentrated in the upper region of thoracic vertebrae, allowing performance of a step of the method of preoperative planning according to an embodiment of the invention.

FIG. 15 shows a lateral patient spine view, with a thoracic kyphosis concentrated in the upper region of thoracic vertebrae, allowing performance of a step of the method of preoperative planning according to an embodiment of the invention. Spine curvature should be changed so as to provide for a closer to zero (or better a close to zero) value of sagittal vertical axis.

The value of lumbar lordosis is on FIG. 15 is 72.1 degrees. The lumbar lordosis is concentrated in the lower region of lumbar vertebrae 2; therefore intermediate marker 8 is closer to end marker 9 than to end marker 7. To change the value of lumbar lordosis, intermediate marker 8 can be moved on the display device by the operator so as to change the curvature of curve C2 between two end markers 7 and 9.

The value of thoracic kyphosis is on FIG. 15 is 61.5 degrees. The thoracic kyphosis is concentrated in the upper region of thoracic vertebrae 2; therefore intermediate marker 5 is closer to end marker 4 than to end marker 6. The thoracic kyphosis should not be so concentrated in the upper region of thoracic vertebrae 2 and should be better distributed. To change the value of thoracic kyphosis, intermediate marker 5 can be moved on the display device by the operator so as to change the curvature of curve C1 between two end markers 4 and 6.

The sagittal vertical axis value E1 is −68.7 mm. This value should be brought close to zero, if possible and while respecting the scheduled values of lumbar lordosis and thoracic kyphosis for this specific patient, so that spine 1 becomes more balanced.

The invention has been described with reference to preferred embodiments. However, many variations are possible within the scope of the invention.

The invention claimed is:

1. A method of preoperative planning to correct spine misalignment of a patient, comprising a step of making a translation and a rotation, in a sagittal plane, of each vertebra of a set of several cervical and/or thoracic and/or lumbar imaged spine vertebrae, so that said set of imaged vertebrae presents afterwards, in the sagittal plane, the same cervical lordosis and/or the same thoracic kyphosis and/or the same lumbar lordosis as a model adapted for said patient,
   wherein it also comprises, before said step of making said translation and said rotation in said sagittal plane a step of making a translation and a rotation, in a coronal plane, of each vertebra of said set of several cervical and/or thoracic and/or lumbar imaged spine vertebrae, so that said set of several cervical and/or thoracic and/or lumbar imaged spine vertebrae becomes straight in said coronal plane, and of making a rotation, in an axial plane, of each vertebra of said set of several cervical and/or thoracic and/or lumbar imaged spine vertebrae, so that said set of several cervical and/or thoracic and/or lumbar imaged spine vertebrae becomes axially aligned.

2. The method of preoperative planning to correct spine misalignment of said patient according to claim 1, wherein said method of preoperative planning to correct spine misalignment of said patient is applied to a set-of several thoracic and several lumbar imaged spine vertebrae of said set of several cervical and/or thoracic and/or lumbar imaged spine vertebrae, so that said set of several thoracic and lumbar imaged spine vertebrae (2)-presents, in the sagittal plane, the same thoracic kyphosis and the same lumbar lordosis as said model adapted for said patient.

3. The method of preoperative planning to correct spine misalignment of said patient according to claim 2, wherein said method of preoperative planning to correct spine misalignment of said patient is applied to all thoracic and all lumbar spine vertebrae of said set of several cervical and/or thoracic and/or lumbar imaged spine vertebrae, so that said patient spine presents, in the sagittal plane, the same thoracic kyphosis and the same lumbar lordosis as said model adapted for said patient.

4. The method of preoperative planning to correct spine misalignment of said patient according to claim 1, wherein:
in said step of making said translation and said rotation in said coronal plane, said translation and rotation are performed simultaneously,
in said step of making said translation and said rotation in said sagittal plane, said translation and rotation are performed simultaneously.

5. The method of preoperative planning to correct spine misalignment of said patient according to claim 1, wherein said method of preoperative planning to correct spine misalignment of said patient also comprises, after said steps of making translations and rotations, a step of pre-twisting at least one rod, to be integrated within said patient body to support said patient spine, according to position and orientation of said set of several cervical and/or thoracic and/or lumbar imaged spine vertebrae after said step of making said translation and said rotation in said sagittal plane.

6. The method of preoperative planning to correct spine misalignment of said patient according to claim 5, wherein in said step of pre-twisting at least one rod, said at least one rod comprises two rods that are pre-twisted which are to be integrated respectively on both sides of said patient spine.

7. The method of preoperative planning to correct spine misalignment of said patient according to claim 1, wherein said method of preoperative planning to correct spine misalignment of said patient also comprises, after said steps of making translations and rotations in said coronal plane and in said sagittal plane, a step of editing a pattern of at least one pre-twisted rod to be integrated within said patient body to support said patient spine, according to position and orientation of said set of several cervical and/or thoracic and/or lumbar imaged spine vertebrae after said step of making said translation and said rotation in said sagittal plane.

8. The method of preoperative planning to correct spine misalignment of said patient according to claim 1, wherein said method of preoperative planning to correct spine misalignment of said patient also comprises, after said steps of making translations and rotations in said coronal plane and in said sagittal plane, a step of calculating the length of at least one rod, to be integrated within said patient body to support said patient spine, according to position and orientation of said set of several cervical and/or thoracic and/or lumbar imaged spine vertebrae after said step of making said translation and said rotation in said sagittal plane.

9. The method of preoperative planning to correct spine misalignment of said patient according to claim 1, wherein a set of several thoracic and/or lumbar imaged spine vertebrae of said set of several cervical and/or thoracic and/or lumbar imaged spine vertebrae is a 3D spine image reconstructed from two 2D radiographic spine images, or alternatively from two 2D radiographic spine images which are a coronal image and a sagittal image.

10. The method of preoperative planning to correct spine misalignment of said patient according to claim 1,
wherein a lumbar lordosis position is obtained by moving two end markers corresponding respectively to higher extreme lumbar vertebra and sacral plate and a lumbar lordosis curvature is obtained by moving an intermediate marker corresponding to an intermediate lumbar vertebra located between both extreme lumbar vertebrae,
and/or wherein a thoracic kyphosis position is obtained by moving two end markers corresponding respectively to both extreme thoracic vertebrae and a thoracic kyphosis curvature is obtained by moving an intermediate marker corresponding to an intermediate thoracic vertebra located between both extreme thoracic vertebrae,
and/or wherein a cervical lordosis position is obtained by moving two end markers corresponding respectively to both extreme cervical vertebrae and a cervical lordosis curvature is obtained by moving an intermediate marker corresponding to an intermediate cervical vertebra located between both extreme cervical vertebrae.

11. The method of preoperative planning to correct spine misalignment of said patient according to claim 1, wherein said model is adapted for said patient first by getting an adapted lordosis from one or more patient based parameters and second by getting an adapted kyphosis from said adapted lordosis and from one or more patient based parameters.

12. The method of preoperative planning to correct spine misalignment of said patient according to claim 11, wherein said adapted lordosis is obtained from patient pelvic incidence and from patient population type and preferably also from patient age.

13. The method of preoperative planning to correct spine misalignment of said patient according to claim 12, wherein said adapted kyphosis is obtained from said adapted lordosis and from patient sagittal vertical axis.

14. The method of preoperative planning to correct spine misalignment of said patient according to claim 13, wherein said adapted kyphosis is obtained by varying said adapted lordosis curvature within a limited range, or alternatively within a limited range of plus or minus 10 degrees, while minimizing said patient sagittal vertical axis.

15. The method of preoperative planning to correct spine misalignment of said patient according to claim 1, wherein said spine misalignment comes from a scoliosis and/or from a degenerative spine.

16. A pre-twisted rod, to be integrated within said patient body to support said patient spine, which has been pre-twisted according to position and orientation of said set of several cervical and/or thoracic and/or lumbar imaged spine vertebrae after a step of making said translation and said rotation in said sagittal plane performed during said method of preoperative planning to correct spine misalignment of said patient according to claim 1.

17. A method of preoperative planning to correct spine misalignment of a patient, comprising a step of making a translation and a rotation, in a sagittal plane, of each vertebra of a set of several cervical and/or thoracic and/or lumbar imaged spine vertebrae, so that said set of imaged vertebrae presents afterwards, in the sagittal plane, the same cervical lordosis and/or the same thoracic kyphosis and/or the same lumbar lordosis as a model adapted for said patient,
wherein it also comprises, before said step of making said translation and said rotation in said sagittal plane a step of making a translation and a rotation, in a coronal plane, of each vertebra of said set of several cervical and/or thoracic and/or lumbar imaged spine vertebrae, so that said set of several cervical and/or thoracic and/or lumbar imaged spine vertebrae becomes straight in said coronal plane, and of making a rotation, in an axial plane, of each vertebra of said set of several cervical and/or thoracic and/or lumbar imaged spine vertebrae, so that said set of several cervical and/or thoracic and/or lumbar imaged spine vertebrae becomes axially aligned; and wherein said method of preoperative planning to correct spine misalignment of said patient also comprises, after said steps of making translations and rotations, a step of pre-twisting at least one rod, to be integrated within said patient body to support said patient spine, according to position and orientation of said set of several cervical and/or thoracic and/or lumbar imaged spine vertebrae after said step of making said translation and said rotation in said sagittal plane.

* * * * *